(12) United States Patent
Ekida et al.

(10) Patent No.: US 7,531,644 B2
(45) Date of Patent: May 12, 2009

(54) IL-6 RECEPTOR•IL-6 DIRECT FUSION PROTEIN

(75) Inventors: Teiji Ekida, Kanagawa (JP); Harutaka Yagame, Iwate (JP); Hiroshi Iida, Kanagawa (JP); Kiyoshi Yasukawa, Kanagawa (JP); Shigeo Tsuchiya, Kanagawa (JP); Teruhiko Ide, Tokyo (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 11/544,639

(22) Filed: Oct. 10, 2006

(65) Prior Publication Data

US 2007/0031376 A1 Feb. 8, 2007

Related U.S. Application Data

(63) Continuation of application No. 10/806,422, filed on Mar. 23, 2004, now abandoned, which is a continuation of application No. 09/743,239, filed as application No. PCT/JP99/03554 on Jul. 1, 1999, now abandoned.

(30) Foreign Application Priority Data

| Jul. 6, 1998 | (JP) | ................................. 10-190597 |
| Jan. 29, 1999 | (JP) | ................................. 11-21788 |
| Apr. 30, 1999 | (JP) | ................................. 11-123411 |

(51) Int. Cl.
*C07K 14/52* (2006.01)
*C07K 14/705* (2006.01)

(52) U.S. Cl. .................... 530/402; 530/350; 530/351
(58) Field of Classification Search .................. None
See application file for complete search history.

(56) References Cited

FOREIGN PATENT DOCUMENTS

| JP | 11-196867 A | 7/1999 |
| WO | WO 99/02552 A2 | 1/1999 |

OTHER PUBLICATIONS

Fischer et al, *Nature Biotechnology*, 15(2):142-145 (1997).
Hollenberg et al, *Current Opinion in Biotechnology*, 8:554-560 (1997).
Mikayama et al, *Proc. Natl. Acad. Sci. USA*, 90:10056-10060 (1993).
Voet et al, *Biochemistry*, John Wiley & Sons, Inc., pp. 126-128 and 228-234 (1990).
Renne et al, *J. Biol. Chem.*, 273(42):27213-27219 (1998).
Jostock et al, *J. of Immunological Methods*, 223(2):171-183 (1999).
Chebath et al, *European Cytokine Network*, John Libbey Eurotext Ltd., Montrouge, Fr., 8(4):359-365 (1997).
Kollet et al, *Blood*, 90(10):394A (1997).

*Primary Examiner*—Prema Mertz
(74) *Attorney, Agent, or Firm*—Sughrue Mion, PLLC

(57) ABSTRACT

The present invention intends to provide an IL-6R•IL-6 fusion protein and the like in which IL-6R and IL-6 are directly linked without a linker.

The IL-6 receptor•IL-6 fusion protein of the present invention has a structure in which one amino acid residue constituting IL-6 receptor and one amino acid residue constituting IL-6 are directly bonded.

6 Claims, 13 Drawing Sheets

SEQUENCE LISTING

<160> NUMBER OF SEQ ID NOS: 79

<210> SEQ ID NO 1
<211> LENGTH: 39
<212> TYPE: DNA
<213> ORGANISM: Artificial Sequence
<220> FEATURE:
<223> OTHER INFORMATION: Annealed Sequence

<400> SEQUENCE: 1 gatccctcc agctggcggt ggtggatccg ccccggtac          39

<210> SEQ ID NO 2
<211> LENGTH: 31
<212> TYPE: DNA
<213> ORGANISM: Artificial Sequence
<220> FEATURE:
<223> OTHER INFORMATION: Annealed Sequence

<400> SEQUENCE: 2
cggggcggat ccaccaccgc cagctggagg g                            31

<210> SEQ ID NO 3
<211> LENGTH: 54
<212> TYPE: DNA
<213> ORGANISM: Artificial Sequence
<220> FEATURE:
<223> OTHER INFORMATION: Annealed Sequence

<400> SEQUENCE: 3
gatcccctcc agctggtggc ggtggctcgg gcggtggtgg gtcggcccg gtac    54

<210> SEQ ID NO 4
<211> LENGTH: 46
<212> TYPE: DNA
<213> ORGANISM: Artificial Sequence
<220> FEATURE:
<223> OTHER INFORMATION: Annealed Sequence

<400> SEQUENCE: 4
cggggccgac ccaccaccgc ccgagccacc gccaccagct ggaggg            46

<210> SEQ ID NO 5
<211> LENGTH: 60
<212> TYPE: DNA
<213> ORGANISM: Artificial Sequence
<220> FEATURE:
<223> OTHER INFORMATION: Annealed Sequence

<400> SEQUENCE: 5
gatcccctcc agctgagaac gaggtgtcca ccccatgca ggcacttcca gccccggtac    60

<210> SEQ ID NO 6
<211> LENGTH: 52
<212> TYPE: DNA
<213> ORGANISM: Artificial Sequence
<220> FEATURE:
<223> OTHER INFORMATION: Annealed Sequence

<400> SEQUENCE: 6
cggggctgga agtgcctgca tgggggtgga cacctcgttc tcagctggag gg    52

<210> SEQ ID NO 7
<211> LENGTH: 54
<212> TYPE: DNA
<213> ORGANISM: Artificial Sequence
<220> FEATURE:
<223> OTHER INFORMATION: Annealed Sequence

<400> SEQUENCE: 7
gatcccctcc agctgagaac gaggtgtcca ccccatgca ggcagccccg gtac    54

<210> SEQ ID NO 8
<211> LENGTH: 46
<212> TYPE: DNA
<213> ORGANISM: Artificial Sequence
<220> FEATURE:
<223> OTHER INFORMATION: Annealed Sequence

<400> SEQUENCE: 8
cggggctgcc tgcatggggg tggacacctc gttctcagct ggaggg    46

<210> SEQ ID NO 9
<211> LENGTH: 24
<212> TYPE: DNA
<213> ORGANISM: Artificial Sequence
<220> FEATURE:
<223> OTHER INFORMATION: Annealed Sequence

<400> SEQUENCE: 9
gatcccctcc agctgccccg gtac    24

<210> SEQ ID NO 10
<211> LENGTH: 16
<212> TYPE: DNA
<213> ORGANISM: Artificial Sequence
<220> FEATURE:
<223> OTHER INFORMATION: Annealed Sequence

<400> SEQUENCE: 10
cggggcagct ggaggg    16

<210> SEQ ID NO 11
<211> LENGTH: 26
<212> TYPE: DNA
<213> ORGANISM: Artificial Sequence
<220> FEATURE:
<223> OTHER INFORMATION: Annealed Sequence

<400> SEQUENCE: 11
aggtggcggt ggatccgccc cggtac    26

<210> SEQ ID NO 12
<211> LENGTH: 22
<212> TYPE: DNA
<213> ORGANISM: Artificial Sequence
<220> FEATURE:
<223> OTHER INFORMATION: Annealed Sequence

<400> SEQUENCE: 12
cggggcggat ccaccgccac ct    22

<210> SEQ ID NO 13
<211> LENGTH: 41
<212> TYPE: DNA
<213> ORGANISM: Artificial Sequence
<220> FEATURE:
<223> OTHER INFORMATION: Annealed Sequence

<400> SEQUENCE: 13
aggtggcggt ggctcgggcg gtggtgggtc ggccccggta c    41

<210> SEQ ID NO 14
<211> LENGTH: 37
<212> TYPE: DNA
<213> ORGANISM: Artificial Sequence
<220> FEATURE:
<223> OTHER INFORMATION: Annealed Sequence

<400> SEQUENCE: 14
cggggccgac ccaccaccgc ccgagccacc gccacct    37

<210> SEQ ID NO 15
<211> LENGTH: 71

```
<212> TYPE: DNA
<213> ORGANISM: Artificial Sequence
<220> FEATURE:
<223> OTHER INFORMATION: Annealed Sequence

<400> SEQUENCE: 15
acttactact aataaagacg atgataatat tggtggcggt ggctcgggcg gtggtgggtc      60
ggccccggta c                                                          71

<210> SEQ ID NO 16
<211> LENGTH: 67
<212> TYPE: DNA
<213> ORGANISM: Artificial Sequence
<220> FEATURE:
<223> OTHER INFORMATION: Annealed Sequence

<400> SEQUENCE: 16
cggggccgac ccaccaccgc ccgagccacc gccaccaata ttatcatcgt ctttattagt      60
agtaagt                                                               67

<210> SEQ ID NO 17
<211> LENGTH: 56
<212> TYPE: DNA
<213> ORGANISM: Artificial Sequence
<220> FEATURE:
<223> OTHER INFORMATION: Annealed Sequence

<400> SEQUENCE: 17
aggtggcggt ggctcgggcg gtggtgggtc gggtggcggc ggatctgccc cggtac         56

<210> SEQ ID NO 18
<211> LENGTH: 52
<212> TYPE: DNA
<213> ORGANISM: Artificial Sequence
<220> FEATURE:
<223> OTHER INFORMATION: Annealed Sequence

<400> SEQUENCE: 18
cggggcagat ccgccgccac ccgacccacc accgcccgag ccaccgccac ct             52

<210> SEQ ID NO 19
<211> LENGTH: 17
<212> TYPE: DNA
<213> ORGANISM: Artificial Sequence
<220> FEATURE:
<223> OTHER INFORMATION: Annealed Sequence

<400> SEQUENCE: 19
aggtggcgcc ccggtac                                                    17

<210> SEQ ID NO 20
<211> LENGTH: 13
<212> TYPE: DNA
<213> ORGANISM: Artificial Sequence
<220> FEATURE:
<223> OTHER INFORMATION: Annealed Sequence

<400> SEQUENCE: 20
cggggcgcca cct                                                        13

<210> SEQ ID NO 21
<211> LENGTH: 23
<212> TYPE: DNA
<213> ORGANISM: Artificial Sequence
<220> FEATURE:
```

-continued

<223> OTHER INFORMATION: Annealed Sequence

<400> SEQUENCE: 21
aggtggcggt ggcgccccgg tac                                           23

<210> SEQ ID NO 22
<211> LENGTH: 19
<212> TYPE: DNA
<213> ORGANISM: Artificial Sequence
<220> FEATURE:
<223> OTHER INFORMATION: Annealed Sequence

<400> SEQUENCE: 22
cggggcgcca ccgccacct                                                19

<210> SEQ ID NO 23
<211> LENGTH: 47
<212> TYPE: DNA
<213> ORGANISM: Artificial Sequence
<220> FEATURE:
<223> OTHER INFORMATION: Annealed Sequence

<400> SEQUENCE: 23
acttactact aataaagacg atgataatat tggtggcgcc ccggtac                 47

<210> SEQ ID NO 24
<211> LENGTH: 43
<212> TYPE: DNA
<213> ORGANISM: Artificial Sequence
<220> FEATURE:
<223> OTHER INFORMATION: Annealed Sequence

<400> SEQUENCE: 24
cggggcgcca ccaatattat catcgtcttt attagtagta agt                     43

<210> SEQ ID NO 25
<211> LENGTH: 53
<212> TYPE: DNA
<213> ORGANISM: Artificial Sequence
<220> FEATURE:
<223> OTHER INFORMATION: Annealed Sequence

<400> SEQUENCE: 25
acttactact aataaagacg atgataatat tggtggcggt ggcgccccgg tac          53

<210> SEQ ID NO 26
<211> LENGTH: 49
<212> TYPE: DNA
<213> ORGANISM: Artificial Sequence
<220> FEATURE:
<223> OTHER INFORMATION: Annealed Sequence

<400> SEQUENCE: 26
cggggcgcca ccgccaccaa tattatcatc gtctttatta gtagtaagt               49

<210> SEQ ID NO 27
<211> LENGTH: 95
<212> TYPE: DNA
<213> ORGANISM: Artificial Sequence
<220> FEATURE:
<223> OTHER INFORMATION: Annealed Sequence

<400> SEQUENCE: 27
acttactact aataaagacg atgataatat tctcttcaga gattctgcaa atgcgacaag   60
cctcccagtg caagattctt cttcagcccc ggtac                              95

<210> SEQ ID NO 28
<211> LENGTH: 91
<212> TYPE: DNA
<213> ORGANISM: Artificial Sequence
<220> FEATURE:
<223> OTHER INFORMATION: Annealed Sequence

<400> SEQUENCE: 28
cggggctgaa gaagaatctt gcactgggag gcttgtcgca tttgcagaat ctctgaagag    60
aatattatca tcgtctttat tagtagtaag t                                  91

<210> SEQ ID NO 29
<211> LENGTH: 86
<212> TYPE: DNA
<213> ORGANISM: Artificial Sequence
<220> FEATURE:
<223> OTHER INFORMATION: Annealed Sequence

<400> SEQUENCE: 29
acttactact aataaagacg atgataatat tctcttcaga gattctgcaa atgcgacaag    60
cctcccagtg caagatgccc cggtac                                        86

<210> SEQ ID NO 30
<211> LENGTH: 82
<212> TYPE: DNA
<213> ORGANISM: Artificial Sequence
<220> FEATURE:
<223> OTHER INFORMATION: Annealed Sequence

<400> SEQUENCE: 30
cggggcatct tgcactggga ggcttgtcgc atttgcagaa tctctgaaga gaatattatc    60 atcgtctttta ttagtagtaa gt                                           82

<210> SEQ ID NO 31
<211> LENGTH: 68
<212> TYPE: DNA
<213> ORGANISM: Artificial Sequence
<220> FEATURE:
<223> OTHER INFORMATION: Annealed Sequence

<400> SEQUENCE: 31
acttactact aataaagacg atgataatat tctcttcaga gattctgcaa atgcgacagc    60
cccggtac                                                            68

<210> SEQ ID NO 32
<211> LENGTH: 64
<212> TYPE: DNA
<213> ORGANISM: Artificial Sequence
<220> FEATURE:
<223> OTHER INFORMATION: Annealed Sequence

<400> SEQUENCE: 32
cggggctgtc gcatttgcag aatctctgaa gagaatatta tcatcgtctt tattagtagt    60
aagt                                                                64

<210> SEQ ID NO 33
<211> LENGTH: 50
<212> TYPE: DNA
<213> ORGANISM: Artificial Sequence
<220> FEATURE:
<223> OTHER INFORMATION: Annealed Sequence

<400> SEQUENCE: 33
acttactact aataaagacg atgataatat tctcttcaga gccccggatc    50

<210> SEQ ID NO 34
<211> LENGTH: 46
<212> TYPE: DNA
<213> ORGANISM: Artificial Sequence
<220> FEATURE:
<223> OTHER INFORMATION: Annealed Sequence

<400> SEQUENCE: 34
cggggctctg aagagaatat tatcatcgtc tttattagta gtaagt    46

<210> SEQ ID NO 35
<211> LENGTH: 41
<212> TYPE: DNA
<213> ORGANISM: Artificial Sequence
<220> FEATURE:
<223> OTHER INFORMATION: Annealed Sequence

<400> SEQUENCE: 35
acttactact aataaagacg atgataatat tgccccggta c    41

<210> SEQ ID NO 36
<211> LENGTH: 37
<212> TYPE: DNA
<213> ORGANISM: Artificial Sequence
<220> FEATURE:
<223> OTHER INFORMATION: Annealed Sequence

<400> SEQUENCE: 36
cggggcaata ttatcatcgt ctttattagt agtaagt    37

<210> SEQ ID NO 37
<211> LENGTH: 26
<212> TYPE: DNA
<213> ORGANISM: Artificial Sequence
<220> FEATURE:
<223> OTHER INFORMATION: Annealed Sequence

<400> SEQUENCE: 37
acttactact aataaagccc cggtac    26

<210> SEQ ID NO 38
<211> LENGTH: 22
<212> TYPE: DNA
<213> ORGANISM: Artificial Sequence
<220> FEATURE:
<223> OTHER INFORMATION: Annealed Sequence

<400> SEQUENCE: 38
cggggcttta ttagtagtaa gt    22

<210> SEQ ID NO 39
<211> LENGTH: 17
<212> TYPE: DNA
<213> ORGANISM: Artificial Sequence
<220> FEATURE:
<223> OTHER INFORMATION: Annealed Sequence

<400> SEQUENCE: 39
acttactgcc ccggtac    17

<210> SEQ ID NO 40
<211> LENGTH: 13

<212> TYPE: DNA
<213> ORGANISM: Artificial Sequence
<220> FEATURE:
<223> OTHER INFORMATION: Annealed Sequence

<400> SEQUENCE: 40
cggggcagta agt                                                          13

<210> SEQ ID NO 41
<211> LENGTH: 38
<212> TYPE: DNA
<213> ORGANISM: Artificial Sequence
<220> FEATURE:
<223> OTHER INFORMATION: Annealed Sequence

<400> SEQUENCE: 41
acttactact aataaagacg atgataatat tccggtac                               38

<210> SEQ ID NO 42
<211> LENGTH: 34
<212> TYPE: DNA
<213> ORGANISM: Artificial Sequence
<220> FEATURE:
<223> OTHER INFORMATION: Annealed Sequence

<400> SEQUENCE: 42
cggaatatta tcatcgtctt tattagtagt aagt                                   34

<210> SEQ ID NO 43
<211> LENGTH: 23
<212> TYPE: DNA
<213> ORGANISM: Artificial Sequence
<220> FEATURE:
<223> OTHER INFORMATION: Annealed Sequence

<400> SEQUENCE: 43
acttactact aataaaccgg tac                                               23

<210> SEQ ID NO 44
<211> LENGTH: 19
<212> TYPE: DNA
<213> ORGANISM: Artificial Sequence
<220> FEATURE:
<223> OTHER INFORMATION: Annealed Sequence

<400> SEQUENCE: 44
cggtttatta gtagtaagt                                                    19

<210> SEQ ID NO 45
<211> LENGTH: 32
<212> TYPE: DNA
<213> ORGANISM: Artificial Sequence
<220> FEATURE:
<223> OTHER INFORMATION: Primer

<400> SEQUENCE: 45
ctcgagaaga ggctggcccc aaggcgctgc cc                                     32

<210> SEQ ID NO 46
<211> LENGTH: 33
<212> TYPE: DNA
<213> ORGANISM: Artificial Sequence
<220> FEATURE:
<223> OTHER INFORMATION: Primer

<400> SEQUENCE: 46
agatctggat tctgtccaag gcgtgcccat ggc                                    33

<210> SEQ ID NO 47
<211> LENGTH: 28
<212> TYPE: DNA
<213> ORGANISM: Artificial Sequence
<220> FEATURE:
<223> OTHER INFORMATION: Primer

<400> SEQUENCE: 47
agatctggta cccccaggag aagattcc                                          28

<210> SEQ ID NO 48
<211> LENGTH: 29
<212> TYPE: DNA
<213> ORGANISM: Artificial Sequence
<220> FEATURE:
<223> OTHER INFORMATION: Primer

<400> SEQUENCE: 48
atgcggccgc tacatttgcc gaagagccc                                         29

<210> SEQ ID NO 49
<211> LENGTH: 51
<212> TYPE: DNA
<213> ORGANISM: Artificial Sequence
<220> FEATURE:
<223> OTHER INFORMATION: Oligomer

<400> SEQUENCE: 49
gatcccctcc agctgagaac gaggtgtcca ccccatgca agcgctggta c                 51

<210> SEQ ID NO 50
<211> LENGTH: 43
<212> TYPE: DNA
<213> ORGANISM: Artificial Sequence
<220> FEATURE:
<223> OTHER INFORMATION: Oilgomer

<400> SEQUENCE: 50
cagcgcttgc atggggtgg acacctcgtt ctcagctgga ggg                          43

<210> SEQ ID NO 51
<211> LENGTH: 33
<212> TYPE: DNA
<213> ORGANISM: Artificial Sequence
<220> FEATURE:
<223> OTHER INFORMATION: Primer

<400> SEQUENCE: 51
ctcgagaaga gggttccccc cgaggagccc cag                                    33

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
tctctagaga atattatcat cg                                                22

<210> SEQ ID NO 53
<211> LENGTH: 29
<212> TYPE: DNA
<213> ORGANISM: Artificial Sequence

```
<220> FEATURE:
<223> OTHER INFORMATION: Primer

<400> SEQUENCE: 53
ctcgagaaga gggagcccca gctctcctg                                    29

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54
tctctagaga atattatcat cg                                           22

<210> SEQ ID NO 55
<211> LENGTH: 24
<212> TYPE: DNA
<213> ORGANISM: Artificial Sequence
<220> FEATURE:
<223> OTHER INFORMATION: Primer

<400> SEQUENCE: 55
tctcgcgatg tagccgcccc acac                                         24

<210> SEQ ID NO 56
<211> LENGTH: 29
<212> TYPE: DNA
<213> ORGANISM: Artificial Sequence
<220> FEATURE:
<223> OTHER INFORMATION: Primer

<400> SEQUENCE: 56
atgcggccgc tacatttgcc gaagagccc                                    29

<210> SEQ ID NO 57
<211> LENGTH: 33
<212> TYPE: DNA
<213> ORGANISM: Artificial Sequence
<220> FEATURE:
<223> OTHER INFORMATION: Primer

<400> SEQUENCE: 57
ctcgagaaga gggttccccc cgaggagccc cag                               33

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
tctctagaga atattatcat cg                                           22

<210> SEQ ID NO 59
<211> LENGTH: 29
<212> TYPE: DNA
<213> ORGANISM: Artificial Sequence
<220> FEATURE:
<223> OTHER INFORMATION: Primer

<400> SEQUENCE: 59
ctcgagaaga gggagcccca gctctcctg                                    29
```

```
<210> SEQ ID NO 60
<211> LENGTH: 13
<212> TYPE: PRT
<213> ORGANISM: Artificial Sequence
<220> FEATURE:
<223> OTHER INFORMATION: Linker

<400> SEQUENCE: 60

Arg Gly Gly Gly Gly Ser Gly Gly Gly Gly Ser Val Glu
 1               5                  10

<210> SEQ ID NO 61
<211> LENGTH: 15
<212> TYPE: PRT
<213> ORGANISM: Artificial Sequence
<220> FEATURE:
<223> OTHER INFORMATION: Linker

<400> SEQUENCE: 61

Gly Gly Gly Gly Ser Gly Gly Gly Gly Ser Gly Gly Gly Gly Ser
 1               5                  10                  15

<210> SEQ ID NO 62
<211> LENGTH: 5
<212> TYPE: PRT
<213> ORGANISM: Artificial Sequence
<220> FEATURE:
<223> OTHER INFORMATION: Linker

<400> SEQUENCE: 62

Ser Ser Glu Leu Val
 1               5

<210> SEQ ID NO 63
<211> LENGTH: 468
<212> TYPE: PRT
<213> ORGANISM: Homo sapiens

<400> SEQUENCE: 63

Met Leu Ala Val Gly Cys Ala Leu Leu Ala Leu Leu Ala Ala Pro
 1               5                  10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
             35                  40                  45

Gly Val Glu Pro Glu Asp Asn Ala Thr Val His Trp Val Leu Arg Lys
         50                  55                  60

Pro Ala Ala Gly Ser His Pro Ser Arg Trp Ala Gly Met Gly Arg Arg
 65                  70                  75                  80

Leu Leu Leu Arg Ser Val Gln Leu His Asp Ser Gly Asn Tyr Ser Cys
                 85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
        130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175
```

```
Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
    370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
    450                 455                 460

Phe Phe Pro Arg
465

<210> SEQ ID NO 64
<211> LENGTH: 212
<212> TYPE: PRT
<213> ORGANISM: Homo sapiens

<400> SEQUENCE: 64

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
```

```
                65                  70                  75                  80
Ser Lys Glu Ala Leu Ala Glu Asn Asn Leu Asn Leu Pro Lys Met Ala
                    85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
                    180                 185                 190

Leu Ile Leu Arg Ser Phe Lys Glu Phe Leu Gln Ser Ser Leu Arg Ala
                195                 200                 205

Leu Arg Gln Met
    210
```

<210> SEQ ID NO 65
<211> LENGTH: 5
<212> TYPE: PRT
<213> ORGANISM: Artificial Sequence
<220> FEATURE:
<223> OTHER INFORMATION: Linker

<400> SEQUENCE: 65

```
Gly Gly Gly Gly Ser
1               5
```

<210> SEQ ID NO 66
<211> LENGTH: 10
<212> TYPE: PRT
<213> ORGANISM: Artificial Sequence
<220> FEATURE:
<223> OTHER INFORMATION: Linker

<400> SEQUENCE: 66

```
Gly Gly Gly Gly Ser Gly Gly Gly Gly Ser
1               5                   10
```

<210> SEQ ID NO 67
<211> LENGTH: 499
<212> TYPE: PRT
<213> ORGANISM: Artificial Sequence
<220> FEATURE:
<223> OTHER INFORMATION: IL-6R - IL-6 fusion protein

<400> SEQUENCE: 67

```
Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
                20                  25                  30

Pro Glu Asp Asn Ala Thr Val His Trp Val Leu Arg Lys Pro Ala Ala
            35                  40                  45

Gly Ser His Pro Ser Arg Trp Ala Gly Met Gly Arg Arg Leu Leu Leu
        50                  55                  60

Arg Ser Val Gln Leu His Asp Ser Gly Asn Tyr Ser Cys Tyr Arg Ala
65                  70                  75                  80
```

```
Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
                100                 105                 110

Cys Glu Trp Gly Pro Arg Ser Thr Pro Ser Leu Thr Thr Lys Ala Val
                115                 120                 125

Leu Leu Val Arg Lys Phe Gln Asn Ser Pro Ala Glu Asp Phe Gln Glu
            130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
                180                 185                 190

Gly Ile Leu Gln Pro Asp Pro Pro Ala Asn Ile Thr Val Thr Ala Val
            195                 200                 205

Ala Arg Asn Pro Arg Trp Leu Ser Val Thr Trp Gln Asp Pro His Ser
            210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
                260                 265                 270

Leu Arg Ala Gln Glu Glu Phe Gly Gln Gly Glu Trp Ser Glu Trp Ser
            275                 280                 285

Pro Glu Ala Met Gly Thr Pro Trp Thr Glu Ser Arg Ser Pro Pro Ala
290                 295                 300

Glu Asn Glu Val Ser Thr Pro Met Gln Ala Ala Pro Val Pro Pro Gly
305                 310                 315                 320

Glu Asp Ser Lys Asp Val Ala Ala Pro His Arg Gln Pro Leu Thr Ser
                325                 330                 335

Ser Glu Arg Ile Asp Lys Gln Ile Arg Tyr Ile Leu Asp Gly Ile Ser
            340                 345                 350

Ala Leu Arg Lys Glu Thr Cys Asn Lys Ser Asn Met Cys Glu Ser Ser
            355                 360                 365

Lys Glu Ala Leu Ala Glu Asn Asn Leu Asn Leu Pro Lys Met Ala Glu
            370                 375                 380

Lys Asp Gly Cys Phe Gln Ser Gly Phe Asn Glu Glu Thr Cys Leu Val
385                 390                 395                 400

Lys Ile Ile Thr Gly Leu Leu Glu Phe Glu Val Tyr Leu Glu Tyr Leu
                405                 410                 415

Gln Asn Arg Phe Glu Ser Ser Glu Glu Gln Ala Arg Ala Val Gln Met
            420                 425                 430

Ser Thr Lys Val Leu Ile Gln Phe Leu Gln Lys Lys Ala Lys Asn Leu
            435                 440                 445

Asp Ala Ile Thr Thr Pro Asp Pro Thr Thr Asn Ala Ser Leu Leu Thr
            450                 455                 460

Lys Leu Gln Ala Gln Asn Gln Trp Leu Gln Asp Met Thr Thr His Leu
465                 470                 475                 480

Ile Leu Arg Ser Phe Lys Glu Phe Leu Gln Ser Ser Leu Arg Ala Leu
            485                 490                 495
```

-continued

Arg Gln Met

<210> SEQ ID NO 68
<211> LENGTH: 489
<212> TYPE: PRT
<213> ORGANISM: Artificial Sequence
<220> FEATURE:
<223> OTHER INFORMATION: IL-6R - IL-6 fusion protein

<400> SEQUENCE: 68

```
Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Ala Pro Val Pro Pro Gly Glu Asp Ser Lys Val Ala Ala Pro His
305                 310                 315                 320

Arg Gln Pro Leu Thr Ser Ser Glu Arg Ile Asp Lys Gln Ile Arg Tyr
                325                 330                 335

Ile Leu Asp Gly Ile Ser Ala Leu Arg Lys Glu Thr Cys Asn Lys Ser
            340                 345                 350

Asn Met Cys Glu Ser Ser Lys Glu Ala Leu Ala Glu Asn Asn Leu Asn
```

-continued

```
                355                 360                 365
Leu Pro Lys Met Ala Glu Lys Asp Gly Cys Phe Gln Ser Gly Phe Asn
    370                 375                 380

Glu Glu Thr Cys Leu Val Lys Ile Ile Thr Gly Leu Leu Glu Phe Glu
385                 390                 395                 400

Val Tyr Leu Glu Tyr Leu Gln Asn Arg Phe Glu Ser Ser Glu Glu Gln
                405                 410                 415

Ala Arg Ala Val Gln Met Ser Thr Lys Val Leu Ile Gln Phe Leu Gln
                420                 425                 430

Lys Lys Ala Lys Asn Leu Asp Ala Ile Thr Thr Pro Asp Pro Thr Thr
            435                 440                 445

Asn Ala Ser Leu Leu Thr Lys Leu Gln Ala Gln Asn Gln Trp Leu Gln
    450                 455                 460

Asp Met Thr Thr His Leu Ile Leu Arg Ser Phe Lys Glu Phe Leu Gln
465                 470                 475                 480

Ser Ser Leu Arg Ala Leu Arg Gln Met
                485

<210> SEQ ID NO 69
<211> LENGTH: 4
<212> TYPE: PRT
<213> ORGANISM: Artificial Sequence
<220> FEATURE:
<223> OTHER INFORMATION: Linker

<400> SEQUENCE: 69

Gly Gly Gly Gly
1

<210> SEQ ID NO 70
<211> LENGTH: 527
<212> TYPE: PRT
<213> ORGANISM: Artificial Sequence
<220> FEATURE:
<223> OTHER INFORMATION: IL-6R - IL-6 fusion protein

<400> SEQUENCE: 70

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
                20                  25                  30

Pro Glu Asp Asn Ala Thr Val His Trp Val Leu Arg Lys Pro Ala Ala
            35                  40                  45

Gly Ser His Pro Ser Arg Trp Ala Gly Met Gly Arg Arg Leu Leu Leu
        50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160
```

-continued

Val Pro Glu Gly Asp Ser Ser Phe Tyr Ile Val Ser Met Cys Val Ala
            165                 170                 175

Ser Ser Val Gly Ser Lys Phe Ser Lys Thr Gln Thr Phe Gln Gly Cys
        180                 185                 190

Gly Ile Leu Gln Pro Asp Pro Pro Ala Asn Ile Thr Val Thr Ala Val
            195                 200                 205

Ala Arg Asn Pro Arg Trp Leu Ser Val Thr Trp Gln Asp Pro His Ser
210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln Asp Ser Ser Ser Ala Pro Val Pro Pro Gly Glu Asp Ser Lys
            340                 345                 350

Asp Val Ala Ala Pro His Arg Gln Pro Leu Thr Ser Ser Glu Arg Ile
        355                 360                 365

Asp Lys Gln Ile Arg Tyr Ile Leu Asp Gly Ile Ser Ala Leu Arg Lys
    370                 375                 380

Glu Thr Cys Asn Lys Ser Asn Met Cys Glu Ser Ser Lys Glu Ala Leu
385                 390                 395                 400

Ala Glu Asn Asn Leu Asn Leu Pro Lys Met Ala Glu Lys Asp Gly Cys
                405                 410                 415

Phe Gln Ser Gly Phe Asn Glu Glu Thr Cys Leu Val Lys Ile Ile Thr
            420                 425                 430

Gly Leu Leu Glu Phe Glu Val Tyr Leu Glu Tyr Leu Gln Asn Arg Phe
        435                 440                 445

Glu Ser Ser Glu Glu Gln Ala Arg Ala Val Gln Met Ser Thr Lys Val
    450                 455                 460

Leu Ile Gln Phe Leu Gln Lys Lys Ala Lys Asn Leu Asp Ala Ile Thr
465                 470                 475                 480

Thr Pro Asp Pro Thr Thr Asn Ala Ser Leu Leu Thr Lys Leu Gln Ala
                485                 490                 495

Gln Asn Gln Trp Leu Gln Asp Met Thr Thr His Leu Ile Leu Arg Ser
            500                 505                 510

Phe Lys Glu Phe Leu Gln Ser Ser Leu Arg Ala Leu Arg Gln Met
        515                 520                 525

<210> SEQ ID NO 71
<211> LENGTH: 524
<212> TYPE: PRT
<213> ORGANISM: Artificial Sequence
<220> FEATURE:
<223> OTHER INFORMATION: IL-6R - IL-6 fusion protein

<400> SEQUENCE: 71

-continued

```
Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
                35                  40                  45

Gly Ser His Pro Ser Arg Trp Ala Gly Met Gly Arg Arg Leu Leu Leu
            50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
            115                 120                 125

Leu Leu Val Arg Lys Phe Gln Asn Ser Pro Ala Glu Asp Phe Gln Glu
130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
            195                 200                 205

Ala Arg Asn Pro Arg Trp Leu Ser Val Thr Trp Gln Asp Pro His Ser
210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
            275                 280                 285

Pro Glu Ala Met Gly Thr Pro Trp Thr Glu Ser Arg Ser Pro Pro Ala
290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln Asp Ala Pro Val Pro Pro Gly Glu Asp Ser Lys Asp Val Ala
            340                 345                 350

Ala Pro His Arg Gln Pro Leu Thr Ser Ser Glu Arg Ile Asp Lys Gln
            355                 360                 365

Ile Arg Tyr Ile Leu Asp Gly Ile Ser Ala Leu Arg Lys Glu Thr Cys
370                 375                 380

Asn Lys Ser Asn Met Cys Glu Ser Ser Lys Glu Ala Leu Ala Glu Asn
385                 390                 395                 400

Asn Leu Asn Leu Pro Lys Met Ala Glu Lys Asp Gly Cys Phe Gln Ser
                405                 410                 415

Gly Phe Asn Glu Glu Thr Cys Leu Val Lys Ile Ile Thr Gly Leu Leu
```

```
                  420                 425                 430
Glu Phe Glu Val Tyr Leu Glu Tyr Leu Gln Asn Arg Phe Glu Ser Ser
            435                 440                 445
Glu Glu Gln Ala Arg Ala Val Gln Met Ser Thr Lys Val Leu Ile Gln
450                 455                 460
Phe Leu Gln Lys Lys Ala Lys Asn Leu Asp Ala Ile Thr Thr Pro Asp
465                 470                 475                 480
Pro Thr Thr Asn Ala Ser Leu Leu Thr Lys Leu Gln Ala Gln Asn Gln
                485                 490                 495
Trp Leu Gln Asp Met Thr Thr His Leu Ile Leu Arg Ser Phe Lys Glu
            500                 505                 510
Phe Leu Gln Ser Ser Leu Arg Ala Leu Arg Gln Met
            515                 520

<210> SEQ ID NO 72
<211> LENGTH: 518
<212> TYPE: PRT
<213> ORGANISM: Artificial Sequence
<220> FEATURE:
<223> OTHER INFORMATION: IL-6R - IL-6 fusion protein

<400> SEQUENCE: 72

Leu Ala Pro Arg Arg Cys Pro Ala Gln Glu Val Ala Arg Gly Val Leu
1               5                   10                  15
Thr Ser Leu Pro Gly Asp Ser Val Thr Leu Thr Cys Pro Gly Val Glu
            20                  25                  30
Pro Glu Asp Asn Ala Thr Val His Trp Val Leu Arg Lys Pro Ala Ala
        35                  40                  45
Gly Ser His Pro Ser Arg Trp Ala Gly Met Gly Arg Arg Leu Leu Leu
    50                  55                  60
Arg Ser Val Gln Leu His Asp Ser Gly Asn Tyr Ser Cys Tyr Arg Ala
65                  70                  75                  80
Gly Arg Pro Ala Gly Thr Val His Leu Leu Val Asp Val Pro Pro Glu
                85                  90                  95
Glu Pro Gln Leu Ser Cys Phe Arg Lys Ser Pro Leu Ser Asn Val Val
            100                 105                 110
Cys Glu Trp Gly Pro Arg Ser Thr Pro Ser Leu Thr Thr Lys Ala Val
        115                 120                 125
Leu Leu Val Arg Lys Phe Gln Asn Ser Pro Ala Glu Asp Phe Gln Glu
    130                 135                 140
Pro Cys Gln Tyr Ser Gln Glu Ser Gln Lys Phe Ser Cys Gln Leu Ala
145                 150                 155                 160
Val Pro Glu Gly Asp Ser Ser Phe Tyr Ile Val Ser Met Cys Val Ala
                165                 170                 175
Ser Ser Val Gly Ser Lys Phe Ser Lys Thr Gln Thr Phe Gln Gly Cys
            180                 185                 190
Gly Ile Leu Gln Pro Asp Pro Ala Asn Ile Thr Val Thr Ala Val
        195                 200                 205
Ala Arg Asn Pro Arg Trp Leu Ser Val Thr Trp Gln Asp Pro His Ser
    210                 215                 220
Trp Asn Ser Ser Phe Tyr Arg Leu Arg Phe Glu Leu Arg Tyr Arg Ala
225                 230                 235                 240
Glu Arg Ser Lys Thr Phe Thr Thr Trp Met Val Lys Asp Leu Gln His
                245                 250                 255
His Cys Val Ile His Asp Ala Trp Ser Gly Leu Arg His Val Val Gln
```

```
                    260                 265                 270
Leu Arg Ala Gln Glu Glu Phe Gly Gln Gly Trp Ser Glu Trp Ser
            275                 280                 285
Pro Glu Ala Met Gly Thr Pro Trp Thr Glu Ser Arg Ser Pro Ala
        290                 295                 300
Glu Asn Glu Val Ser Thr Pro Met Gln Ala Leu Thr Thr Asn Lys Asp
305                 310                 315                 320
Asp Asp Asn Ile Leu Phe Arg Asp Ser Ala Asn Ala Thr Ala Pro Val
                325                 330                 335
Pro Pro Gly Glu Asp Ser Lys Asp Val Ala Ala Pro His Arg Gln Pro
            340                 345                 350
Leu Thr Ser Ser Glu Arg Ile Asp Lys Gln Ile Arg Tyr Ile Leu Asp
            355                 360                 365
Gly Ile Ser Ala Leu Arg Lys Glu Thr Cys Asn Lys Ser Asn Met Cys
        370                 375                 380
Glu Ser Ser Lys Glu Ala Leu Ala Glu Asn Asn Leu Asn Leu Pro Lys
385                 390                 395                 400
Met Ala Glu Lys Asp Gly Cys Phe Gln Ser Gly Phe Asn Glu Glu Thr
                405                 410                 415
Cys Leu Val Lys Ile Ile Thr Gly Leu Leu Glu Phe Glu Val Tyr Leu
                420                 425                 430
Glu Tyr Leu Gln Asn Arg Phe Glu Ser Ser Glu Glu Gln Ala Arg Ala
            435                 440                 445
Val Gln Met Ser Thr Lys Val Leu Ile Gln Phe Leu Gln Lys Lys Ala
        450                 455                 460
Lys Asn Leu Asp Ala Ile Thr Thr Pro Asp Pro Thr Thr Asn Ala Ser
465                 470                 475                 480
Leu Leu Thr Lys Leu Gln Ala Gln Asn Gln Trp Leu Gln Asp Met Thr
                485                 490                 495
Thr His Leu Ile Leu Arg Ser Phe Lys Glu Phe Leu Gln Ser Ser Leu
                500                 505                 510
Arg Ala Leu Arg Gln Met
        515

<210> SEQ ID NO 73
<211> LENGTH: 512
<212> TYPE: PRT
<213> ORGANISM: Artificial Sequence
<220> FEATURE:
<223> OTHER INFORMATION: IL-6R - IL-6 fusion protein

<400> SEQUENCE: 73

Leu Ala Pro Arg Arg Cys Pro Ala Gln Glu Val Ala Arg Gly Val Leu
1               5                   10                  15
Thr Ser Leu Pro Gly Asp Ser Val Thr Leu Thr Cys Pro Gly Val Glu
            20                  25                  30
Pro Glu Asp Asn Ala Thr Val His Trp Val Leu Arg Lys Pro Ala Ala
        35                  40                  45
Gly Ser His Pro Ser Arg Trp Ala Gly Met Gly Arg Arg Leu Leu Leu
    50                  55                  60
Arg Ser Val Gln Leu His Asp Ser Gly Asn Tyr Ser Cys Tyr Arg Ala
65                  70                  75                  80
Gly Arg Pro Ala Gly Thr Val His Leu Leu Val Asp Val Pro Pro Glu
                85                  90                  95
Glu Pro Gln Leu Ser Cys Phe Arg Lys Ser Pro Leu Ser Asn Val Val
```

-continued

```
                100                 105                 110
Cys Glu Trp Gly Pro Arg Ser Thr Pro Ser Leu Thr Thr Lys Ala Val
            115                 120                 125

Leu Leu Val Arg Lys Phe Gln Asn Ser Pro Ala Glu Asp Phe Gln Glu
130                 135                 140

Pro Cys Gln Tyr Ser Gln Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
                195                 200                 205

Ala Arg Asn Pro Arg Trp Leu Ser Val Thr Trp Gln Asp Pro His Ser
            210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
                260                 265                 270

Leu Arg Ala Gln Glu Glu Phe Gly Gln Gly Glu Trp Ser Glu Trp Ser
            275                 280                 285

Pro Glu Ala Met Gly Thr Pro Trp Thr Glu Ser Arg Ser Pro Pro Ala
290                 295                 300

Glu Asn Glu Val Ser Thr Pro Met Gln Ala Leu Thr Thr Asn Lys Asp
305                 310                 315                 320

Asp Asp Asn Ile Leu Phe Arg Ala Pro Val Pro Gly Glu Asp Ser
                325                 330                 335

Lys Asp Val Ala Ala Pro His Arg Gln Pro Leu Thr Ser Ser Glu Arg
                340                 345                 350

Ile Asp Lys Gln Ile Arg Tyr Ile Leu Asp Gly Ile Ser Ala Leu Arg
            355                 360                 365

Lys Glu Thr Cys Asn Lys Ser Asn Met Cys Glu Ser Ser Lys Glu Ala
        370                 375                 380

Leu Ala Glu Asn Asn Leu Asn Leu Pro Lys Met Ala Glu Lys Asp Gly
385                 390                 395                 400

Cys Phe Gln Ser Gly Phe Asn Glu Glu Thr Cys Leu Val Lys Ile Ile
                405                 410                 415

Thr Gly Leu Leu Glu Phe Glu Val Tyr Leu Glu Tyr Leu Gln Asn Arg
            420                 425                 430

Phe Glu Ser Ser Glu Glu Gln Ala Arg Ala Val Gln Met Ser Thr Lys
                435                 440                 445

Val Leu Ile Gln Phe Leu Gln Lys Lys Ala Lys Asn Leu Asp Ala Ile
        450                 455                 460

Thr Thr Pro Asp Pro Thr Thr Asn Ala Ser Leu Leu Thr Lys Leu Gln
465                 470                 475                 480

Ala Gln Asn Gln Trp Leu Gln Asp Met Thr Thr His Leu Ile Leu Arg
                485                 490                 495

Ser Phe Lys Glu Phe Leu Gln Ser Ser Leu Arg Ala Leu Arg Gln Met
            500                 505                 510
```

<210> SEQ ID NO 74

<211> LENGTH: 509
<212> TYPE: PRT
<213> ORGANISM: Artificial Sequence
<220> FEATURE:
<223> OTHER INFORMATION: IL-6R - IL-6 fusion protein

<400> SEQUENCE: 74

```
Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
305                 310                 315                 320

Asp Asp Asn Ile Ala Pro Val Pro Pro Gly Glu Asp Ser Lys Asp Val
                325                 330                 335

Ala Ala Pro His Arg Gln Pro Leu Thr Ser Ser Glu Arg Ile Asp Lys
            340                 345                 350

Gln Ile Arg Tyr Ile Leu Asp Gly Ile Ser Ala Leu Arg Lys Glu Thr
        355                 360                 365

Cys Asn Lys Ser Asn Met Cys Glu Ser Ser Lys Glu Ala Leu Ala Glu
    370                 375                 380
```

```
Asn Asn Leu Asn Leu Pro Lys Met Ala Glu Lys Asp Gly Cys Phe Gln
385                 390                 395                 400

Ser Gly Phe Asn Glu Glu Thr Cys Leu Val Lys Ile Ile Thr Gly Leu
                405                 410                 415

Leu Glu Phe Glu Val Tyr Leu Glu Tyr Leu Gln Asn Arg Phe Glu Ser
            420                 425                 430

Ser Glu Glu Gln Ala Arg Ala Val Gln Met Ser Thr Lys Val Leu Ile
                435                 440                 445

Gln Phe Leu Gln Lys Lys Ala Lys Asn Leu Asp Ala Ile Thr Thr Pro
        450                 455                 460

Asp Pro Thr Thr Asn Ala Ser Leu Leu Thr Lys Leu Gln Ala Gln Asn
465                 470                 475                 480

Gln Trp Leu Gln Asp Met Thr Thr His Leu Ile Leu Arg Ser Phe Lys
                485                 490                 495

Glu Phe Leu Gln Ser Ser Leu Arg Ala Leu Arg Gln Met
                500                 505
```

<210> SEQ ID NO 75
<211> LENGTH: 504
<212> TYPE: PRT
<213> ORGANISM: Artificial Sequence
<220> FEATURE:
<223> OTHER INFORMATION: IL-6R - IL-6 fusion protein

<400> SEQUENCE: 75

```
Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
                20                  25                  30

Pro Glu Asp Asn Ala Thr Val His Trp Val Leu Arg Lys Pro Ala Ala
            35                  40                  45

Gly Ser His Pro Ser Arg Trp Ala Gly Met Gly Arg Arg Leu Leu Leu
        50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240
```

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Ala
305                 310                 315                 320

Pro Val Pro Pro Gly Glu Asp Ser Lys Asp Val Ala Ala Pro His Arg
                325                 330                 335

Gln Pro Leu Thr Ser Ser Glu Arg Ile Asp Lys Gln Ile Arg Tyr Ile
            340                 345                 350

Leu Asp Gly Ile Ser Ala Leu Arg Lys Glu Thr Cys Asn Lys Ser Asn
        355                 360                 365

Met Cys Glu Ser Ser Lys Glu Ala Leu Ala Glu Asn Asn Leu Asn Leu
    370                 375                 380

Pro Lys Met Ala Glu Lys Asp Gly Cys Phe Gln Ser Gly Phe Asn Glu
385                 390                 395                 400

Glu Thr Cys Leu Val Lys Ile Ile Thr Gly Leu Leu Glu Phe Glu Val
                405                 410                 415

Tyr Leu Glu Tyr Leu Gln Asn Arg Phe Glu Ser Ser Glu Glu Gln Ala
            420                 425                 430

Arg Ala Val Gln Met Ser Thr Lys Val Leu Ile Gln Phe Leu Gln Lys
        435                 440                 445

Lys Ala Lys Asn Leu Asp Ala Ile Thr Thr Pro Asp Pro Thr Thr Asn
    450                 455                 460

Ala Ser Leu Leu Thr Lys Leu Gln Ala Gln Asn Gln Trp Leu Gln Asp
465                 470                 475                 480

Met Thr Thr His Leu Ile Leu Arg Ser Phe Lys Glu Phe Leu Gln Ser
                485                 490                 495

Ser Leu Arg Ala Leu Arg Gln Met
            500

<210> SEQ ID NO 76
<211> LENGTH: 501
<212> TYPE: PRT
<213> ORGANISM: Artificial Sequence
<220> FEATURE:
<223> OTHER INFORMATION: IL-6R - IL-6 fusion protein

<400> SEQUENCE: 76

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

```
Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
            115                 120                 125

Leu Leu Val Arg Lys Phe Gln Asn Ser Pro Ala Glu Asp Phe Gln Glu
            130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
            165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
            195                 200                 205

Ala Arg Asn Pro Arg Trp Leu Ser Val Thr Trp Gln Asp Pro His Ser
            210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
            245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
            275                 280                 285

Pro Glu Ala Met Gly Thr Pro Trp Thr Glu Ser Arg Ser Pro Pro Ala
            290                 295                 300

Glu Asn Glu Val Ser Thr Pro Met Gln Ala Leu Thr Ala Pro Val Pro
305                 310                 315                 320

Pro Gly Glu Asp Ser Lys Asp Val Ala Ala Pro His Arg Gln Pro Leu
            325                 330                 335

Thr Ser Ser Glu Arg Ile Asp Lys Gln Ile Arg Tyr Ile Leu Asp Gly
            340                 345                 350

Ile Ser Ala Leu Arg Lys Glu Thr Cys Asn Lys Ser Asn Met Cys Glu
            355                 360                 365

Ser Ser Lys Glu Ala Leu Ala Glu Asn Asn Leu Asn Leu Pro Lys Met
            370                 375                 380

Ala Glu Lys Asp Gly Cys Phe Gln Ser Gly Phe Asn Glu Glu Thr Cys
385                 390                 395                 400

Leu Val Lys Ile Ile Thr Gly Leu Leu Glu Phe Glu Val Tyr Leu Glu
            405                 410                 415

Tyr Leu Gln Asn Arg Phe Glu Ser Ser Glu Glu Gln Ala Arg Ala Val
            420                 425                 430

Gln Met Ser Thr Lys Val Leu Ile Gln Phe Leu Gln Lys Lys Ala Lys
            435                 440                 445

Asn Leu Asp Ala Ile Thr Thr Pro Asp Pro Thr Thr Asn Ala Ser Leu
450                 455                 460

Leu Thr Lys Leu Gln Ala Gln Asn Gln Trp Leu Gln Asp Met Thr Thr
465                 470                 475                 480

His Leu Ile Leu Arg Ser Phe Lys Glu Phe Leu Gln Ser Ser Leu Arg
            485                 490                 495

Ala Leu Arg Gln Met
            500
```

<210> SEQ ID NO 77
<211> LENGTH: 508
<212> TYPE: PRT
<213> ORGANISM: Artificial Sequence
<220> FEATURE:
<223> OTHER INFORMATION: IL-6R - IL-6 fusion protein

<400> SEQUENCE: 77

```
Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
305                 310                 315                 320

Asp Asp Asn Ile Pro Val Pro Gly Glu Asp Ser Lys Asp Val Ala
                325                 330                 335

Ala Pro His Arg Gln Pro Leu Thr Ser Ser Glu Arg Ile Asp Lys Gln
            340                 345                 350

Ile Arg Tyr Ile Leu Asp Gly Ile Ser Ala Leu Arg Lys Glu Thr Cys
        355                 360                 365
```

-continued

```
Asn Lys Ser Asn Met Cys Glu Ser Ser Lys Glu Ala Leu Ala Glu Asn
    370                 375                 380

Asn Leu Asn Leu Pro Lys Met Ala Glu Lys Asp Gly Cys Phe Gln Ser
385                 390                 395                 400

Gly Phe Asn Glu Glu Thr Cys Leu Val Lys Ile Ile Thr Gly Leu Leu
                405                 410                 415

Glu Phe Glu Val Tyr Leu Glu Tyr Leu Gln Asn Arg Phe Glu Ser Ser
                420                 425                 430

Glu Glu Gln Ala Arg Ala Val Gln Met Ser Thr Lys Val Leu Ile Gln
            435                 440                 445

Phe Leu Gln Lys Lys Ala Lys Asn Leu Asp Ala Ile Thr Thr Pro Asp
    450                 455                 460

Pro Thr Thr Asn Ala Ser Leu Leu Thr Lys Leu Gln Ala Gln Asn Gln
465                 470                 475                 480

Trp Leu Gln Asp Met Thr Thr His Leu Ile Leu Arg Ser Phe Lys Glu
                485                 490                 495

Phe Leu Gln Ser Ser Leu Arg Ala Leu Arg Gln Met
                500                 505

<210> SEQ ID NO 78
<211> LENGTH: 503
<212> TYPE: PRT
<213> ORGANISM: Artificial Sequence
<220> FEATURE:
<223> OTHER INFORMATION: IL-6R - IL-6 fusion protein

<400> SEQUENCE: 78

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
                20                  25                  30

Pro Glu Asp Asn Ala Thr Val His Trp Val Leu Arg Lys Pro Ala Ala
            35                  40                  45

Gly Ser His Pro Ser Arg Trp Ala Gly Met Gly Arg Arg Leu Leu Leu
        50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
    210                 215                 220
```

```
Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
            245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
            275                 280                 285

Pro Glu Ala Met Gly Thr Pro Trp Thr Glu Ser Arg Ser Pro Pro Ala
            290                 295                 300

Glu Asn Glu Val Ser Thr Pro Met Gln Ala Leu Thr Thr Asn Lys Pro
305                 310                 315                 320

Val Pro Pro Gly Glu Asp Ser Lys Asp Val Ala Ala Pro His Arg Gln
                325                 330                 335

Pro Leu Thr Ser Ser Glu Arg Ile Asp Lys Gln Ile Arg Tyr Ile Leu
            340                 345                 350

Asp Gly Ile Ser Ala Leu Arg Lys Glu Thr Cys Asn Lys Ser Asn Met
            355                 360                 365

Cys Glu Ser Ser Lys Glu Ala Leu Ala Glu Asn Asn Leu Asn Leu Pro
370                 375                 380

Lys Met Ala Glu Lys Asp Gly Cys Phe Gln Ser Gly Phe Asn Glu Glu
385                 390                 395                 400

Thr Cys Leu Val Lys Ile Ile Thr Gly Leu Leu Glu Phe Glu Val Tyr
                405                 410                 415

Leu Glu Tyr Leu Gln Asn Arg Phe Glu Ser Ser Glu Glu Gln Ala Arg
            420                 425                 430

Ala Val Gln Met Ser Thr Lys Val Leu Ile Gln Phe Leu Gln Lys Lys
            435                 440                 445

Ala Lys Asn Leu Asp Ala Ile Thr Thr Pro Asp Pro Thr Thr Asn Ala
            450                 455                 460

Ser Leu Leu Thr Lys Leu Gln Ala Gln Asn Gln Trp Leu Gln Asp Met
465                 470                 475                 480

Thr Thr His Leu Ile Leu Arg Ser Phe Lys Glu Phe Leu Gln Ser Ser
                485                 490                 495

Leu Arg Ala Leu Arg Gln Met
            500

<210> SEQ ID NO 79
<211> LENGTH: 498
<212> TYPE: PRT
<213> ORGANISM: Artificial Sequence
<220> FEATURE:
<223> OTHER INFORMATION: IL-6R - IL-6 fusion protein

<400> SEQUENCE: 79

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80
```

-continued

Gly Arg Pro Ala Gly Thr Val His Leu Leu Val Asp Val Pro Pro Glu
            85                  90                  95

Glu Pro Gln Leu Ser Cys Phe Arg Lys Ser Pro Leu Ser Asn Val Val
        100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
                180                 185                 190

Gly Ile Leu Gln Pro Asp Pro Pro Ala Asn Ile Thr Val Thr Ala Val
            195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
                260                 265                 270

Leu Arg Ala Gln Glu Glu Phe Gly Gln Gly Glu Trp Ser Glu Trp Ser
    275                 280                 285

Pro Glu Ala Met Gly Thr Pro Trp Thr Glu Ser Arg Ser Pro Pro Ala
290                 295                 300

Glu Asn Glu Val Ser Thr Pro Met Gln Ala Leu Val Pro Pro Gly Glu
305                 310                 315                 320

Asp Ser Lys Asp Val Ala Ala Pro His Arg Gln Pro Leu Thr Ser Ser
                325                 330                 335

Glu Arg Ile Asp Lys Gln Ile Arg Tyr Ile Leu Asp Gly Ile Ser Ala
                340                 345                 350

Leu Arg Lys Glu Thr Cys Asn Lys Ser Asn Met Cys Glu Ser Ser Lys
                355                 360                 365

Glu Ala Leu Ala Glu Asn Asn Leu Asn Leu Pro Lys Met Ala Glu Lys
    370                 375                 380

Asp Gly Cys Phe Gln Ser Gly Phe Asn Glu Glu Thr Cys Leu Val Lys
385                 390                 395                 400

Ile Ile Thr Gly Leu Leu Glu Phe Glu Val Tyr Leu Glu Tyr Leu Gln
                405                 410                 415

Asn Arg Phe Glu Ser Ser Glu Glu Gln Ala Arg Ala Val Gln Met Ser
                420                 425                 430

Thr Lys Val Leu Ile Gln Phe Leu Gln Lys Lys Ala Lys Asn Leu Asp
            435                 440                 445

Ala Ile Thr Thr Pro Asp Pro Thr Thr Asn Ala Ser Leu Leu Thr Lys
450                 455                 460

-continued

```
Leu Gln Ala Gln Asn Gln Trp Leu Gln Asp Met Thr Thr His Leu Ile
465                 470                 475                 480

Leu Arg Ser Phe Lys Glu Phe Leu Gln Ser Ser Leu Arg Ala Leu Arg
                485                 490                 495

Gln Met
```

IL-6 RECEPTOR•IL-6 DIRECT FUSION PROTEIN

CROSS-REFERENCE TO RELATED APPLICATIONS

This application is a Continuation of U.S. application Ser. No. 10/806,422, filed Mar. 23, 2004 now abandoned; which is a Continuation of U.S. application Ser. No. 09/743,239, filed Jan. 5, 2001 now abandoned; which is a 371 of PCT/JP99/03554, filed Jul. 1, 1999; the disclosure of each of which is incorporated herein by reference.

TECHNICAL FIELD

The present invention relates to a fusion protein composed of an interleukin-6 receptor (hereinafter referred to as IL-6R) and an interleukin-6 (hereinafter referred to as IL-6) directly linked without a linker sequence; a gene for coding for the fusion protein; a host transformed by an expression vector containing the gene; a method of cultivating the host; a process for purifying the fusion protein derived from the culture of the host; a novel ex vivo amplifier containing the fusion protein for hematopoietic stem cells; and a novel blood platelet-proliferating agent.

BACKGROUND TECHNIQUE

IL-6, IL-11, ciliary neurotropic factors, leukemia inhibitory factors, oncostatin-M, and cardiotropin-1 belonging to IL-6 type cytokines are known to transmit signals through a receptor complex containing at least one signal-transmitting protein gp130. For example, IL-6 links to IL-6R, and the resulting IL-6•IL-6R complex contains gp130.

The hematopoiesis system is one of the living body protection systems in which IL-6 plays an important role. The process for expression of IL-6R in hematopoietic cells is different between human cells and mouse cells. Undifferentiated human hematopoietic precursor cells which can form a granulocyte macrophage colony, an erythroblast colony, a megakaryocyte colony, and a mixed colony thereof on a methylcellulose culture do not express a sufficient amount of IL-6R (Tajima et al.: J. Exp. Med. 184, 1996). Therefore, the undifferentiated human hematopoietic precursor cell is almost unreactive to IL-6, whereas it is strongly reactive to an IL-6•IL-6R complex. In contrast, the undifferentiated mouse hematopoietic precursor cell expresses a sufficient amount of IL-6R. Nakahata, and the inventors of the present invention found that the human megakaryocyte precursor cell does not express a sufficient amount of IL-6 (Japanese Patent Application No. 9-325847). These findings are consistent with the fact that IL-6 administered to a mouse increases significantly the number of blood platelets and the IL-6 administered to a human body is limited in its effect.

The linking constant between IL-6 and soluble IL-6R is reported to be $5 \times 10^{-9}$ M (Yasukawa et al.: J. Biochem. vol. 108, p. 673, 1990). This means, that in a mixture of 200 ng/mL ($1 \times 10^{-8}$ M) of IL-6 (mw: 20000) with 500 ng/mL ($1 \times 10^{-8}$ M) of soluble IL-6R (mw: 50000), half of the molecules will exist in an unlinked state. Actually, soluble IL-6R is required in an amount of 1000 ng/mL or more to react it with cells not expressing IL-6R.

By genetic engineering, two kinds of proteins existing independently in nature can be fused into a fusion protein of one polypeptide chain. When two kinds of proteins linkable with each other are expressed as a fusion protein, presumably the bonding is strong and dissociation is less liable to occur as long as the respective proteins in the fused state can keep the inherent structures (biologically active structure)

For two kinds of proteins in a fused protein to take the inherent structures, steric hindrance should not be caused between the two proteins. Further, the two proteins in the fused protein having the inherent structures should have freedom degrees for contacting each other. Therefore, a linker is employed conventionally for fusion of the proteins: the linker being a sequence of 5-20 amino acid residues such as a glycine residue and a serine residue having a high freedom degree for linking of two proteins. By such indirect fusion of proteins through a linker not related to the fused proteins, the steric hindrance between the two proteins is avoided and the freedom degree for the linking is achieved.

For example, for expression of a fusion protein by bonding a V domain of an H chain with a V domain of an L chain of antibodies affinitive for bonding, a linker sequence is disclosed which has a residue sequence of GGGGSGGGGSGGGGS (G: glycine residue, S: serine residue) (SEQ ID NO:61) (Houston et al.: Proc. Natl. Acad. Sci. USA, 85, p. 5879, 1988).

Fusion proteins were prepared recently from IL-6 and IL-6R linkable to each other with a linker (illustrated in FIG. 1(a)). One is a fusion protein prepared in a manner such that an irrelevant linker RGGGGSGGGGSVE (SEQ ID NO:60) not contained in IL-6 and IL-6R is bonded to the C-terminal 323th alanine residue in IL-6R, and IL-6 is bonded to its C terminal side (Fisher et al.: Nature Biotech, 15, p. 142, 1997). A second one is a fusion protein prepared in a manner such that a linker EFM (E: glutamic acid residue, F: phenylalanine residue, and M: methionine residue) is bonded to the C-terminal 356th valine residue of IL-6R, and further IL-6 is bonded to its C terminal side (Chebath et al.: Eur. Cytokine Netw, 8, p. 359, 1997). The inventors of the present invention discovered a fusion protein prepared by bonding a linker SSELV (L: leucine residue, V: valine residue) (SEQ ID NO:62) to the C-terminal 334th leucine residue of IL-6R, and further bonding IL-6 to the C-terminal thereof (Japanese patent Application No. 10-2921).

Generally, it is known that a foreign protein expressed by genetic recombination can be cleaved by a naturally expressed protease in the host. Therefore, the fusion protein IL-6R•IL-6 having expressed may also be cleaved by protease in the host. In particular, the yeast *Pichia pastoris* is known to express various proteases. However, the aforementioned reports do not describe this matter. If the fusion protein IL-6R•IL-6 is cleaved by a protease expressed in the host, preparation of a fusion protein IL-6R•IL-6 resistant to the cleavage enables production of a larger amount of the fusion protein IL-6R•IL-6 from the culture of the yeast *Pichia pastoris* or other host.

A fusion protein like IL-6R•IL-6, which can maintains firmly the fused state of two proteins, is expected to be particularly effective in a fused state as a medicine in signal transmission system of IL-6 in a human body or a like animal.

In development of a fusion protein as a periodically dosed medicine, high possibility of the aforementioned immune reaction is a problem, since the linker is not contained in the proteins and irrelevant to them, and has an independent steric structure. Therefore, the linker has preferably a sequence as short as possible, or nonuse of the linker is desirable.

As described above, for constituting the fusion protein, the two constituting proteins should not cause steric hindrance between them, and should have freedom for linking together. For example, for direct fusion of IL-6R and IL-6 without using a linker without causing steric hindrance with a freedom degree for linking together, many factors should be decided such as the order of the proteins in fusion, the amino acid residue in the N-terminal side protein and the that in the C-terminal side protein.

As the fusion protein of IL-6R with IL-6, only three examples mentioned above have been reported which employ a linker, and the fusion necessarily requires a linker. FIG. 1(a) illustrates a fusion protein in which two proteins are linked together through a linker. The direct linking without the linker has not been reported yet.

The present invention intends to provide a IL-6R•IL-6 fusion protein in which IL-6R and IL-6 are linked directly without a linker as illustrated in FIG. 1(b). The present invention intends also to provide an IL-6R•IL-6 fusion protein which is resistant to cleaving action of the protease expressed by a host, especially a *Pichia pastoris* type yeast, and a gene for coding for the fusion protein.

DISCLOSURE OF THE INVENTION

To achieve the above objects, after comprehensive investigation on IL-6R•IL-6 fusion protein, the inventors of the present invention completed a fusion protein having IL-6R at the N-terminal side and IL-6 at the C-terminal side linked without employing a linker therebetween. The present invention relates to an IL-6R•IL-6 fusion protein in which one amino acid residue constituting IL-6R and one amino acid residue constituting IL-6 are directly bonded. Further, the inventors of the present invention found that lysine of the 37th residue from the N-terminal of IL-6 can be cleaved by protease at its C-terminal side, and has completed a protease-resistant IL-6R•IL-6 fusion protein by modification at the protease-cleavable site, especially an IL-6R•IL-6 fusion protein in which IL-6 with deletion of 10 amino acid residues from 28th alanine residue to 37th lysine residue of the N-terminal side of the IL-6R is linked to C-terminal of the IL-6R, and also completed a gene for coding for it.

The present invention provides also a gene for coding for IL-6R•IL-6 fusion protein in which one amino acid residue of IL-6R and one amino acid residue of IL-6 are linked directly.

The present invention further provides a yeast of *Pichia pastoris* species which is transformed by an expression vector containing a gene for coding for IL-6R•IL-6 fusion protein in which one amino acid residue of IL-6R and one amino acid residue of IL-6 are linked directly.

The present invention still further provides a process for producing an IL-6R•IL-6 fusion protein, comprising a step of cultivating in a culture medium a yeast of a *Pichia pastoris* species having been transformed by an expression vector containing a gene for coding for an IL-6R•IL-6 fusion protein in which one amino acid residue of IL-6R and one amino acid residue of IL-6 are linked directly; and a step of collecting the IL-6R•IL-6 fusion protein as a secretory protein from the culture medium.

The present invention still further provides a process for producing an IL-6R•IL-6 fusion protein, comprising cultivating a yeast of a *Pichia pastoris* species having been transformed by an expression vector containing a gene for coding for an IL-6R•IL-6 fusion protein in which one amino acid residue of IL-6R and one amino acid residue of IL-6 are linked directly, in a culture medium of natural origin containing a carbon source and no methanol, and adding methanol during progress of the cultivation.

The present invention still further provides a process for producing an IL-6R•IL-6 fusion protein, comprising subjecting a solution containing an IL-6R•IL-6 fusion protein, in which one amino acid residue of IL-6R and one amino acid residue of IL-6 are directly linked, to three steps of chromatography including ion-exchange chromatography, hydrophobic chromatography, and gel-filtration chromatography to collect the IL-6R•IL-6 fusion protein.

The present invention still further provides an ex vivo amplifier for a hematopoietic stem cells, comprising an IL-6R•IL-6 fusion protein in which one amino acid residue of IL-6R and one amino acid residue of IL-6 are directly linked.

The present invention still further provides a blood platelet growing agent containing as a main component an IL-6R•IL-6 fusion protein in which one amino acid residue of IL-6R and one amino acid residue of IL-6 are directly linked. The present invention is described below in detail.

The fusion protein of the present invention is characterized in that IL-6R is placed at the N-terminal side of the fusion protein, and IL-6 is placed at the C-terminal side thereof, and the two proteins are linked directly without a linker. For improving the resistance to the protease as mentioned above, the two protein may be linked by a polypeptide linker. However, in view of lower antigenicity in medicine dose, preferred is the direct linking without polypeptide linker. When the useful linker includes known linker sequences (Fisher et al.: Nature Biotech, 15, p. 142, 1997; and Chebath et al.: Eur. Cytokine Netw, 8, p. 142, 1997), or in another example thereof, to the C-terminal 344th leucine residue position of IL-6R, a linker composed of serine residue/serine residue/glutamic acid residue/leucine residue/valine residue is linked, and further to the C-terminal side thereof, IL-6 is linked. The IL-6R constituting the IL-6R-IL-6 of the present invention is a membrane protein having 468 amino acid residues in full length (SEQ ID NO:63), and comprises a signal region, an extracellular region, a transmembrane region, and an intracellular region (Yamasaki et al.: Science, 241, p. 825, 1988). In human IL-6R, it is presumed that the signal region ranges from the methionine residue at the first position of the N-terminal to about the alanine residue at 19th position; the extracellular region ranges from about the leucine residue at the 20th position to about the aspartic acid residue at the 358th position; the transmembrane region ranges from about the serine residue at 359th position to about the leucine residue at the 386th position; and the intracellular region ranges from about arginine residue at the 387th position to about the arginine residue at 468th position. The extracellular region is classified into an immunoglobulin-like domain and a cytokine receptor domain, presumably the immunoglobulin-like domain ranging from about the leucine residue at the 20th position to the aspartic acid residue at the 111th position, and the cytokine receptor domain ranging from about the valine residue at about the 112th position to about the alanine residue at the 323th position.

In the IL-6R, it is known that the domain essential to the linking to IL-6 is the cytokine receptor domain and the immunoglobulin-like domain is not necessary. The cytokine receptor domain is a structure constituted of two short barrel-shaped structure, each composed of seven β-sheets (Yawata et al.: EMBO J., 12, p. 1705, 1993).

In the present invention, not only the IL-6R in full length is useful, but also the entire of the extracellular region, or the cytokine receptor region, namely a part of the IL-6R is useful. This is because the cytokine region can constitute the signal transmission system by combining with the IL-6, and the extracellular region includes that domain.

According to the information acquired by the inventors of the present invention, specific examples of the N-terminal of IL-6R are the leucine residue at the 20th position, the valine residue at the 112th position, and the glutamic acid residue at the 116th position from the N-terminal.

Further, according to the information acquired by the inventors of the present invention, specific examples of the C-terminal of IL-6R are any one of 39 amino acid residues in the range from the N-terminal 323th alanine residue to the 361th serine residue; preferably any one of the six amino acid of the 323th alanine residue, the 333th alanine residue, the 334th leucine residue, the 335th threonine residue, the lysine 338th residue, and the 343th isoleucine residue. To the C-terminal side of the fraction of the IL-6R, the N-terminal of IL-6 is linked. The N-terminal of the IL-6R may be deleted appropriately in consideration of the effects in the signal transmission of the fusion protein.

The IL-6 constituting the IL-6R•IL-6 fusion protein is a secretory protein composed of 212 amino acid residues in full length (SEQ ID NO:64) having four α-helixes (Hirano et al.: Nature, 324, vol. 731, 1986). The four a-helixes are known to be all necessary for the activity of the IL-6. Therefore, the IL-6 used in the present invention is not specially limited, provided that it has all of the four helixes. In other words, not only the full length of the IL-6 is useful, but also a partial IL-6 in which a part of amino acids at the N-terminal or the C-terminal are deleted can be useful. An example of the partial IL-6 is the one having a sequence from the N-terminal 28th alanine residue or the 29th proline residue to the N-terminal 212th methionine residue, which is known as the structure of the secretory IL-6. Otherwise, a sequence of the partial IL-6 may be decided by reference to examples of expression of IL-6 (e.g., Yasukawa et al.: Biotech. Lett., 12, p. 419, 1990), or examples of expression of IL-6R•IL-6 fusion protein (Fischer et al.: Nature Biotech., 15, p. 142, 1997).

With the fusion protein made protease-resistant by introducing modification at the protease-cleaving site in the primary structure, the modification and the site thereof is decided suitably to meet the kind of the protease having different cleaving sites: the site of deletion of the amino acid, the site of addition of foreign amino acid residue, or the site of substitution of the amino acid to be resistant to the cleavage by the protease. In the modification by substitution, the inherent steric configuration is changed by substitution not to be cleaved or to be less liable to be cleaved by a protease. In the substitution, the intended amino acid is substituted preferably by a smaller-sized amino acid such as glycine and serine. In the modification by the deletion, the protein molecule is modified by deletion of the intended amino acid to prevent the recognition of the cleavage site by the protease, or to change the inherent steric configuration not to be cleaved or to be less liable to be cleaved.

The modification can be introduced by genetic engineering to a gene for coding for the IL-6R•IL-6 fusion protein. The modification may be any of deletion of an amino acid, insertion of an amino acid, and substitution of an amino acid. Of the modifications, deletion of an amino acid or amino acid sequence at or around the protease cleavage site is particularly preferred, since the operation therefor is relatively easy and the influence of substitution of the non-inherent amino acid on the antigenicity or other properties is considered to be less.

In genetic production of the IL-6R•IL-6 fusion protein of the present invention, the specific standard of the selection is impartation of resistance to protease secreted by the host cell employed. More specifically, as shown later in Examples, the IL-6R•IL-6 fusion protein to be produced genetically is expressed in a selected host cells, and the expressed product is subjected to purification by a conventional liquid chromatography or other purification process. In the purification process, the substance of the peak which seems to be the decomposition product by the protease is collected, or in an SDS-PAGE method, the substance of the band which seems to be the decomposition product by the protease is collected. The N-terminal amino acid sequence is analyzed to find the cleaved site of the IL-6R•IL-6 fusion protein cleaved by the protease secreted by the selected host cells.

After detection of the site cleaved by the protease of the IL-6R•IL-6 fusion protein in the primary structure, the IL-6R•IL-6 fusion protein which is resistant to the protease can be obtained by deletion of the amino acid residues around the cleaved site or other modification method so as not to be cleaved or to be less liable to be cleaved by the protease.

Further, the protease-resistant IL-6R•IL-6 fusion protein of the present invention is useful for retaining the biological activity of IL-6R•IL-6 fusion protein in a medicine for a longer time in the presence of a protease. For producing the IL-6R•IL-6 fusion protein of this purpose, the protease which can maintain the activity in the environment for exhibiting a biological activity of the IL-6R•IL-6 fusion protein is obtained, the site of cleavage of the unmodified IL-6R•IL-6 fusion protein by the protease is detected, and the site is modified as described above.

The IL-6R•IL-6 fusion protein modified as above is preferably tested for confirmation of the retention of its biological activity after the modification. For the confirmation, the modified IL-6R•IL-6 fusion protein is prepared, and is tested, for instance, as shown later in Example by use of a BAF130 cell strain. If the modified IL-6R•IL-6 fusion protein is found to be not biologically active in this confirmation, another modification is introduced, and the confirmation is conducted again in the same manner as above.

Further, the modified IL-6R•IL-6 fusion protein is preferably tested for confirmation of its resistance to the protease. For this confirmation, the modified IL-6R•IL-6 fusion protein is allowed to coexist with the protease for a certain time, and the protein is analyzed, for instance, by combination of the SDS-PAGE and the western blotting. If the protein is found to be not resistant to the protease, another modification is introduced, and the confirmation is conducted again in the same manner as above. The IL-6R•IL-6 fusion protein, which has been made resistant to the protease secreted by the host cells has been imparted, is produced by use of the same host cells, and the confirmation test is conducted with the cell culture in the same manner as above.

The IL-6R•IL-6 fusion protein of the present invention can readily be produced with a gene for coding for it by a gene recombination technique. The gene for coding for the IL-6R or IL-6 has already been isolated, and the base sequence is well known. Therefore, the fusion protein of the present invention can be produced by preparing the necessary gene sequences from the amino acid sequences of the IL-6R and the IL-6, and linking them by use of a restriction enzyme. Instead of employing the natural gene sequence, a codon therein may be replaced by another codon which codes for the same amino acid residue but has a different base sequence in consideration of the codon condensation. This is because the use of a specific codon can sometimes improves the expression ratio or the translation ratio in expression of a protein by gene recombination.

The host for production of the fusion protein of the present invention by gene recombination is not limited specially, and *Escherichia coli*, or an animal cells typified by CHO cells usually employed in gene recombination operation may be used according to literature (Yasukawa et al.: J. Biotech., 108, p. 673, 1990). Of the hosts, Pichia pastoris yeast employed in Examples is particularly preferred since this yeast is capable of growing with methanol as the only carbon source, and can be cultivated at a low cost in comparison with the animal cells like CHO cells.

An example of the IL-6R•IL-6 fusion protein resistant to the protease secreted by the yeast of Pichia pastoris species which is a suitable host cells in genetic production of the IL-6R•IL-6 fusion protein is the one derived from an IL-6R with a modified IL-6 in which at least the sequence from the N-terminal 28th alanine residue to the N-terminal 37th lysine residue is deleted. The protease-resistant IL-6R•IL-6 fusion protein of the present invention can be mass-produced by preparing a gene for coding for the protease-resistant IL-6R•IL-6 fusion protein, preparing an expression vector having the gene incorporated therein, transforming the host cells, and cultivating the transformed host cells. The IL-6R•IL-6 fusion protein made resistant to protease secreted by the host cells as described above is not cleaved or hardly cleaved by the protease after it is expressed in the host cells. Therefore, it can readily be produced in a larger amount in comparison with the non-resistant IL-6R•IL-6 fusion protein.

The above-described gene for producing the fusion protein of the present invention prepared by gene recombination technique is incorporated into an expression vector to introduce it into the host (for transformation). Into the expression vector, an expression-controlling gene, a gene for selecting the transformed host, and so forth are incorporated in addition to the aforementioned gene. The genes to be incorporated are selected suitably depending on the host employed. For instance, when the yeast of Pichia pastoris strain is used as the host, there are introduced the upstream sequence and the downstream sequence of an alcohol oxidase gene for introduction of the gene for coding for the IL-6R•IL-6 fusion protein in chromosomal DNA, a histidine synthesis gene as a selection indicator, and a promotor sequence of an alcohol oxidase gene for expression control; and when E. coli is used as the host, there are introduced an ampicillin-resistant gene as a selection indicator, and a Lac promotor/operator sequence. A commercial expression vector (e.g., pPIC9, an expression vector for the Pichia pastoris strain yeast, produced by Invitrogen Co.) can be used by introducing the gene of the present invention.

In the present invention, when the Pichia pastoris strain yeast is transformed by an expression vector containing a gene for coding for the IL-6R•IL-6 fusion protein for the production of the fusion protein, are preferably incorporated, into the expression vector, the inherent signal peptide of IL-6R and a signal peptide of α-factor as the signal peptide of the fusion protein, especially a signal peptide of the α-factor for high expression.

The fusion protein can be produced by cultivating the aforementioned transformed host under suitable conditions and causing expression of the fusion protein in relation to the expression-controlling gene in the expression vector as necessary. In an example of the present invention, a jar fermenter is used when employing preferably Pichia pastoris yeast as the host. Specifically, a preliminarily prepared 20% glycerol-frozen yeast of Pichia pastoris strain capable of expressing the IL-6R•IL-6 fusion protein is inoculated into a 100 mL of a culture contained in a 500-mL shaking flask. The yeast is cultivated at 28-30° C. for 20 hours. The resulting 100-mL liquid culture is inoculated into a 6-9 L of culture contained in a 16-L jar fermenter, and is cultivated at 28-30° C. with aeration and stirring. For monitoring the state of the cultivated yeast, the OD600, the pH, the dissolved oxygen concentration, stirring rate, and the temperature are preferably monitored and controlled. The culture medium is not limited, provided that a carbon source of natural origin is contained. Specific compositions are shown in Examples. A commercial jar fermenter may be used for the cultivation. During the cultivation, methanol is added when the glycerol has been consumed totally. The consumption of the glycerol is detected by monitoring the dissolved oxygen. The methanol is preferably added within five hours after the complete consumption. An excessive amount of methanol is toxic to the yeast, whereas the deficiency of methanol suppresses the function of the promoter sequence of the alcohol oxidase gene. Therefore, the amount of the methanol is preferably not less than 0.5% and not more than 5% (weight/volume).

The fusion protein produced by the cultivation is collected from the culture by a suitable method. In the case where Escherichia coli is employed as the host, the expressed fusion protein is accumulated as insoluble granules in the E. coli cells, so that the E. coli mass is crushed and subjected to refolding or purification under suitable conditions. In the case where the Pichia pastoris yeast is employed as the host, the fusion protein can be obtained by purification from the supernatant liquid of the culture. The material solution for purification is not limited, provided that it contains the fusion protein. An example of the liquid is a liquid culture of Pichia pastoris yeast containing the fusion protein. The solution may be treated as it is, but may be treated after dilution with a buffer solution or pure water, or after concentration by ultrafiltration or by use of ammonium sulfate. The purification may be conducted by liquid chromatography. Preferably three types of chromatography, ion-exchange chromatography, hydrophobic chromatography, and gel filtration chromatography may be employed in combination.

The supernatant liquid culture of Pichia pastoris yeast, since it is voluminous, is preferably treated firstly by ion-exchange chromatography. The ion-exchange chromatography includes cation chromatography and anion chromatography, and either may employed suitably in consideration of protein removal efficiency. For example, in the cation chromatography, SP is used as the cation exchange functional group; and in the anion chromatography, DEAE is used and the anion exchange functional group. In consideration of the flow rate of 100 mL/min or higher and the nature of the sample solution not treated with a filtered of 1 µm or a smaller pore size, a preferred example is the cation chromatography employing a fluidized adsorption bed, Stream line SP C-50 column (produced by Amasham Pharmacia Co.). The fraction containing the fusion protein obtained above is then subjected to hydrophobic chromatography to obtain a fraction containing the fusion protein of a higher purity. This fraction is concentrated by cation chromatography to conduct efficiently the subsequent gel filtration chromatography as shown later in Examples.

The inventors of the present invention investigated comprehensively the stem cell amplification effect of the IL-6R•IL-6 fusion protein in which one of the amino acid residues of the IL-6R and one of the amino acid residues of IL-6 are linked directly. As the results, it was found that, in cultivation of CD34-positive cells on a methylcellulose plate in the presence of the fusion protein and a stem cell factor (SCF), the colony-forming ability is increased remarkably in comparison with the reported one in cultivation in the presence of IL-6, IL-6R, and SCF. The present invention is accomplished based on ex vivo amplification of hematopoietic stem cells by the IL-6R•IL-6 fusion protein in which one of the amino acid residues of IL-6R and one of the amino acid residues of IL-6 are linked directly. The present invention relates to an ex vivo amplifying agent for the hematopoietic stem cells, and an ex vivo amplifying method for the hematopoietic stem cells by employing the IL-6R•IL-6 fusion protein.

The fusion protein of the present invention is effective by itself to a certain extent as an ex vivo amplifying agent for hematopoietic stem cells, and is valuable practically. The effect is made remarkable by addition of any one of cytokines stimulating tyrosine kinase such as SCF, and FLK2 ligand, particularly SCF. Further, interleukin-3 (IL-3) or a platelet proliferation factor (TPO) may be added thereto. The hematopoietic stem cells can be obtained from umbilical blood, peripheral blood, or bone marrow by CD34 selection as a fraction containing the hematopoietic stem cells. The fusion protein of the present invention can be supplied as a kit comprising vials containing separately the fusion protein of the present invention and another cytokine, or may be supplied as a mixture thereof contained in one vial. The ex vivo amplification of the hematopoietic stem cell can be conducted by cultivating a fraction containing the hematopoietic cells in a serum-free culture containing the fusion protein of the present invention, and SCF or the like at 37° C. for 1-3 weeks in a vessel like a plastic bag. The amplified hematopoietic stem cells can be returned to a patient in the same manner as the conventional peripheral blood stem cell transfusion.

The inventors of the present invention investigated comprehensively the blood platelet proliferation effect of the IL-6R•IL-6 fusion protein in which one of the amino acid residues of the IL-6R and one of the amino acid residues of IL-6 are linked directly. Consequently, as shown later in Example, it was found that, in the mouse dosed with the fusion protein, proliferation of blood platelets is significantly promoted, and that, in the mouse preliminarily dosed with a carcinostatic agent and dosed with the fusion protein, the recovery of the platelets is accelerated significantly. The present invention is based on the newly found effects on proliferation or recovery of blood platelets by the fusion protein in which one of the amino acid residues of IL-6R and one of the amino acid residues of IL-6 are linked directly. The present invention relates also to a blood platelet-proliferating agent containing the fusion protein as the main component, and a method for proliferating the platelets with the agent. The blood platelet-proliferating agent of the present invention is preferably dosed by parenteral administration such as intravenous administration, intramuscular administration, and percutaneous administration. The amount of the dose is decided depending on the kind of the disease causing the blood platelet deficiency, the state of the patient, and so forth, generally ranging from 1 to 500 μg/kg/day. The agent is dosed periodically depending on the state of proliferation of the blood platelets. The blood platelet-proliferating agent of the present invention can be formulated by mixing a conventional vehicle or an activator such as a physiological saline, a glucose solution, mannitol, methylcellulose, gelatin, and human serum albumin. The blood platelet-proliferating agent of the present invention may be freeze-dried. The freeze-dried product is redissolved before use in an isotonic solution such as a physiological saline, a glucose solution, and a Ringer's solution.

BRIEF DESCRIPTION OF THE DRAWINGS

In FIG. 6, amp denotes an ampicillin-tolerant gene; ori, a transcription initiation site; HIS4, a histidine-synthesizing gene; 3'AOXTT, a terminator; IL-6, an IL-6 gene; IL-6R, an IL-6R gene; S, a gene for coding for a signal sequence; and 5'AOX1, an upstream region of an alcohol oxidase gene containing a promoter sequence.

In FIG. 6, MeOH conc. signifies a methanol concentration (unit: % (wt/vol)); EIA signifies sandwich immunoassay, and Bio Assay signifies a biological activity.

In FIG. 10, the lane of symbol H shows the simple endoglycosidase H, and the lanes denoted by the numerals 0 to 180 show the results of PF6 treated with the endoglycosidase H for the time (minutes) denoted by the numeral respectively. The bar marks denoted by the numerals 97.4 and 66.3 show respectively the position of detection of the molecular weight marker (molecular weight of 97.4 kDa, or 66.3 kDa).

In FIG. 11, G denotes a granulocyte colony; M, a macrophage colony; GM, a granulocyte/macrophage mixed colony; Blast, a blast colony; Mix, a granulocyte/macrophage/erythroblast mixed colony; and BFU-E, an erythroblast colony.

In FIG. 12, the asterisk shows a significant difference from the blood platelet number from that of Group 1 ($P<0.05$).

In FIG. 13, the asterisk shows a significant difference from the blood platelet number from that of Group 1 ($P<0.05$).

BEST MODE FOR PRACTICING THE INVENTION

Examples are shown below for explaining the invention in more detail. However, the present invention is not limited by the Examples.

EXAMPLE 1

Preparation of Intermediate Plasmids

Intermediate plasmids pBS6RS and pBS6RL were prepared by inserting an oligonucleotide coding for a linker for the purpose of preparing a gene (cDNA) coding for an IL-6R-IL-6 fusion protein linked through a linker as below.

Firstly, a cloning vector, pBluescript II KS(-) (produced by Toyobo Co.), was cut by a restriction enzyme, KpnI, treated with a Klenow fragment, and subjected to ligation reaction to obtain plasmid pBS with the KpnI site deleted.

Then IL-6R gene (cDNA) was amplified by using a primer p6RAB20L (SEQ ID NO:45) and a primer p6RF320S (SEQ ID NO:46), and was cut by XhoI. This was inserted into pBS having preliminarily been cut by XhoI and EcoRV to obtain pBS6R.

Figure 1:
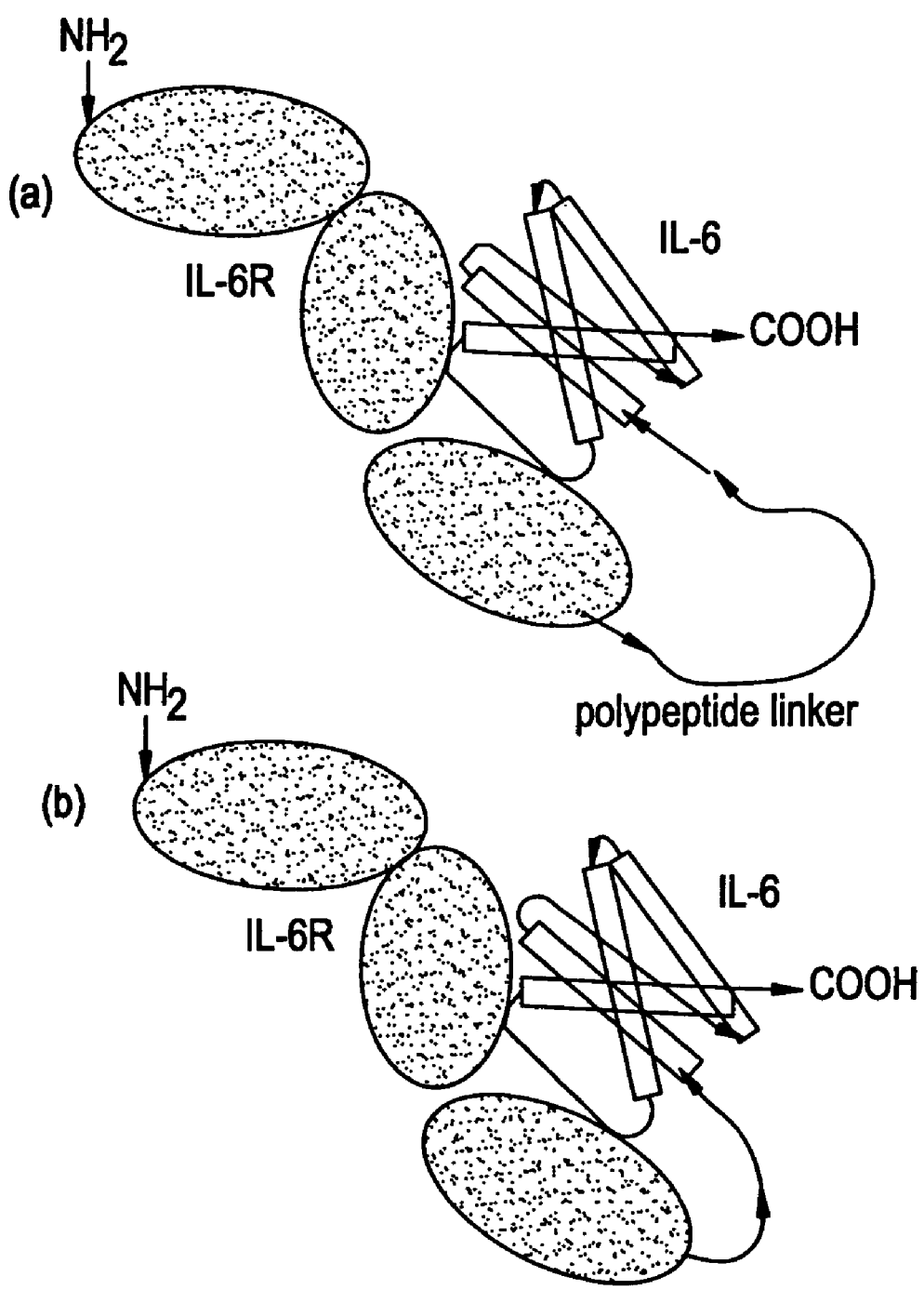
FIG. 1(a) illustrates an IL-6R•IL-6 fusion protein formed by linking IL-6R with IL-6 through a linker sequence.
FIG. 1(b) illustrates an IL-6R•IL-6 fusion protein formed by linking IL-6R with IL-6 directly without a linker.
Figure 2:
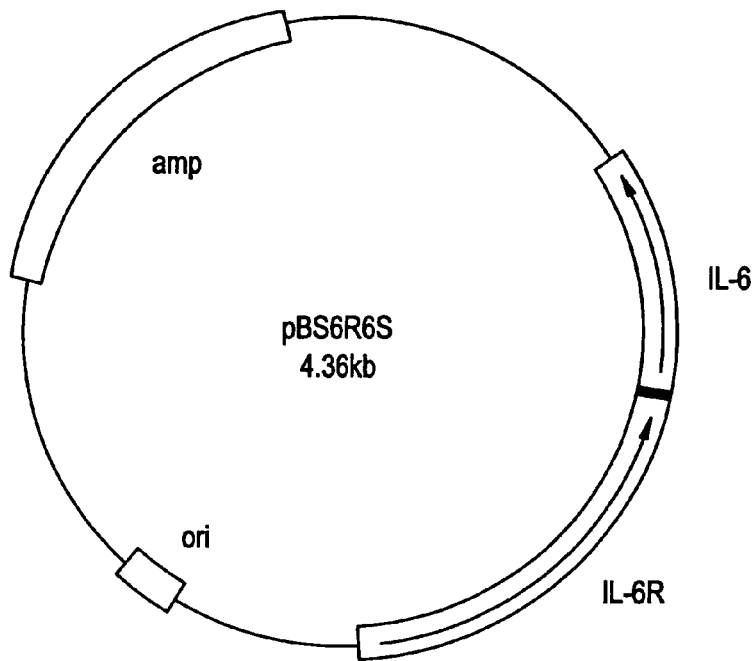
FIG. 2 shows the structure of the plasmid pBS6R6S prepared in Example 1, in which amp denotes an ampicillin-tolerant gene, ori denotes a transcription initiation site, IL-6 denotes an IL-6 gene, and IL-6R denotes an IL-6R gene.
Figure 3:
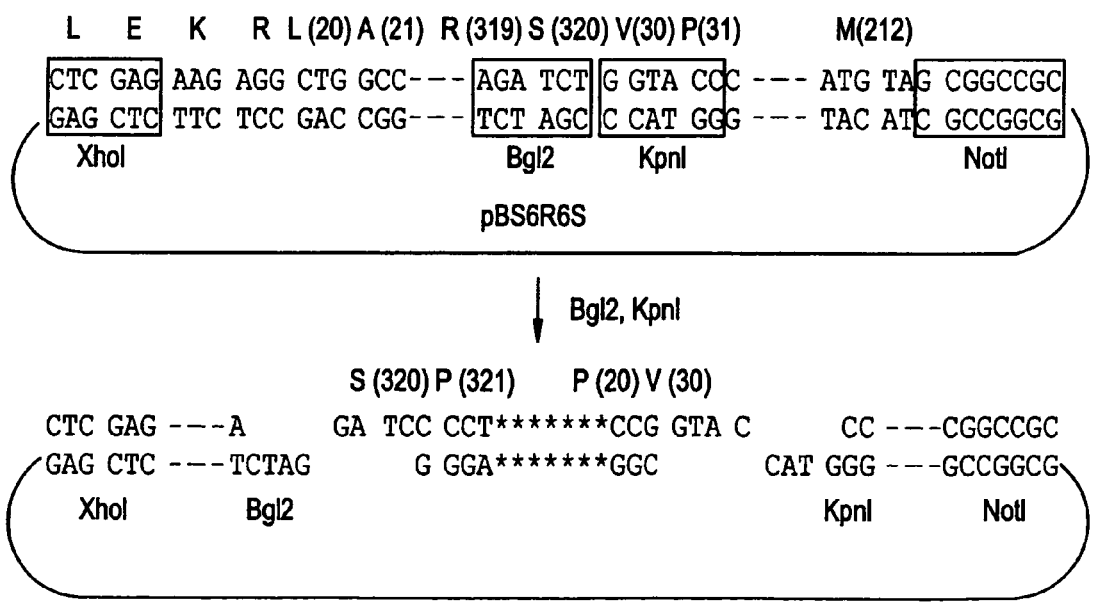
FIG. 3 shows the procedure of insertion of two kinds of annealed oligonucleotides into the plasmid pBS6R6S shown in FIG. 2 by the method shown in Example 2.

IL-6 gene (cDNA) was amplified by using a primer pIL6B2 (SEQ ID NO:47) and a primer pIL6F (SEQ ID NO:48), and was cut by Bgl II and NotI. This was inserted into a plasmid pBS6R having preliminarily been cut by Bgl II and NotI to obtain pBS6R6S. FIG. 2 shows the structure of the obtained pBS6R6S.

Figure 4:
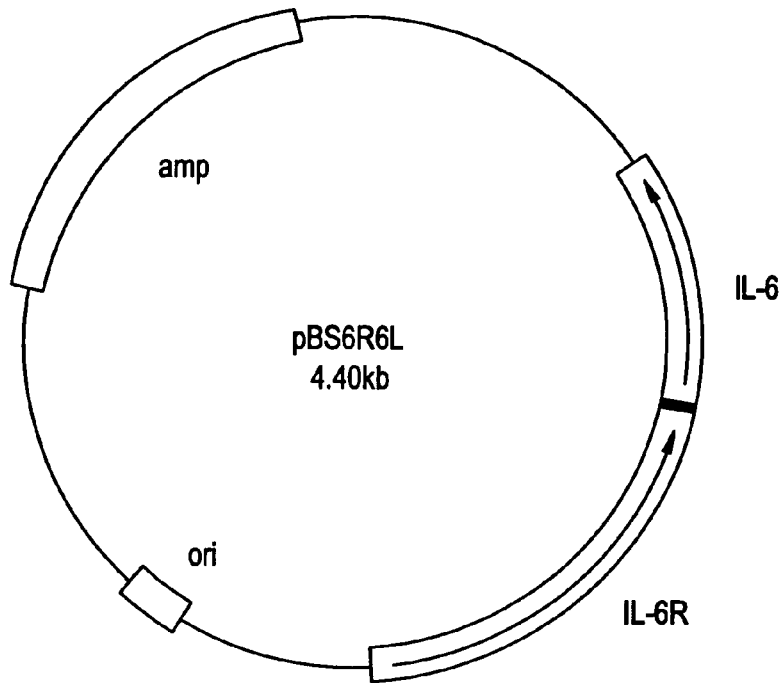
FIG. 4 shows the structure of the plasmid pBS6R6L prepared in Example 1, in which amp denotes an ampicillin-tolerant gene, ori denotes a transcription initiation site, IL-6 denotes an IL-6 gene, and IL-6R denotes an IL-6R gene.
Figure 5:
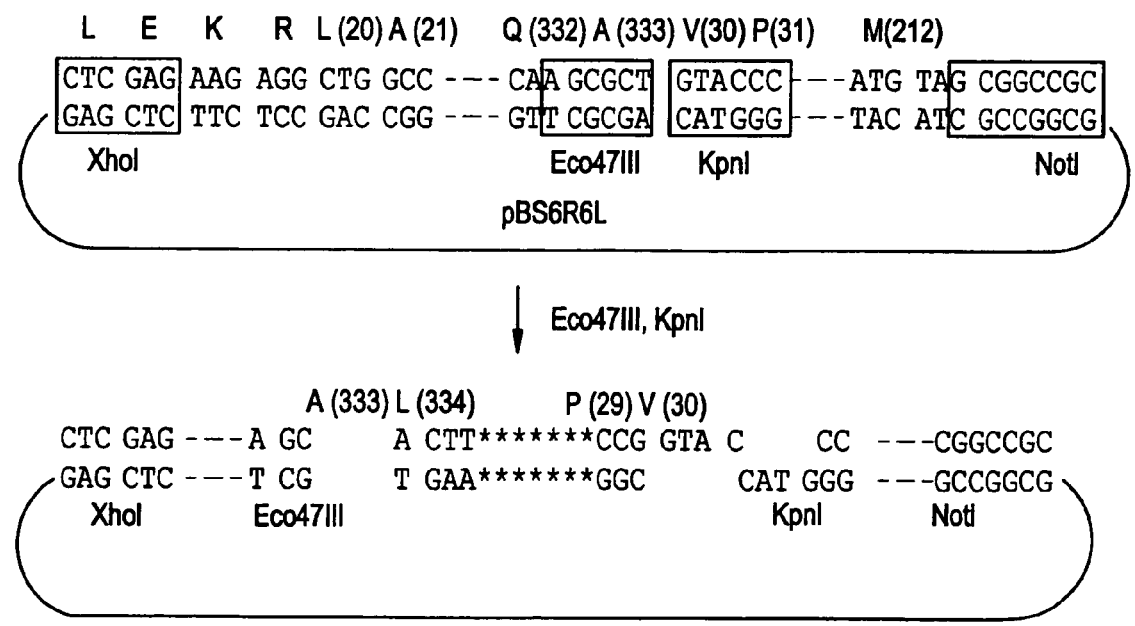
FIG. 5 shows the procedure of insertion of two kinds of annealed oligonucleotides into the plasmid pBS6R6L shown in FIG. 4 by the method shown in Example 2.

Then, an oligomers 320S333Ab (SEQ ID NO:49) and 320S333Af (SEQ ID NO:50) were annealed in a conventional manner. This was inserted into the plasmid pBS6R6S having preliminarily been cut by Bgl II and Kpn I to obtain pBS6R6L. FIG. 4 shows the structure of the obtained pBS6R6L.

EXAMPLE 2

Preparation of Expression Plasmids

Into pBS6R6S having preliminarily been cut by Bgl II and KpnI, Annealed Sequences 1-5 obtained by annealing two kinds of oligonucleotides were respectively inserted as shown below to obtain five kinds of plasmids having as an insert a gene for coding for the IL-6R•IL-6 fusion protein.

Annealed Sequence 1 (323AG4SA): The oligonucleotide of SEQ ID NO:1 is at the sense side, and the oligonucleotide of SEQ ID NO:2 is at the antisense side.

Annealed Sequence 2 (323AG4S2A): The oligonucleotide of SEQ ID NO:3 is at the sense side, and the oligonucleotide of SEQ ID NO:4 is at the antisense side.

Annealed Sequence 3 (334LPA): The oligonucleotide of SEQ ID NO:5 is at the sense side, and the oligonucleotide of SEQ ID NO:6 is at the antisense side.

Annealed Sequence 4 (333AΔA): The oligonucleotide of SEQ ID NO:7 is at the sense side, and the oligonucleotide of SEQ ID NO:8 is at the antisense side.

Annealed Sequence 5 (323AΔA): The oligonucleotide of SEQ ID NO:9 is at the sense side, and the oligonucleotide of SEQ ID NO:10 is at the antisense side.

Annealed Sequence 1 (323AG4SA) expresses a fusion protein formed by linking the N-terminal 323th alanine of IL-6R and the N-terminal 28th alanine of IL-6 through a linker GGGGS (SEQ ID NO:65). Annealed Sequence 2 (323AG4S2A) expresses a fusion protein formed by linking the N-terminal 323th alanine of IL-6R and the N-terminal 28th alanine of IL-6 through a linker GGGGSGGGGS (SEQ ID NO:66). Annealed Sequence 3 expresses a fusion protein formed by linking the N-terminal 334th leucine of IL-6R and the N-terminal 28th alanine of IL-6 through a linker P. Annealed Sequence 4 (333AΔA) expresses a fusion protein of the present invention formed by directly linking the N-terminal 333th alanine of IL-6R and the N-terminal 28th alanine of IL-6 without a linker (SEQ ID NO:67). Annealed Sequence 5 (323AΔA) expresses a fusion protein of the present invention formed by directly linking the N-terminal 323th alanine of IL-6R and the N-terminal 28th alanine of IL-6 without a linker (SEQ ID NO:68).

Next, into pBS6R6L having preliminarily been cut by Eco47 III and KpnI, Annealed Sequences 6-22 obtained by annealing two kinds of oligonucleotides are respectively inserted as shown below to obtain 17 kinds of plasmids having a gene as an insert for coding for the IL-6R•IL-6 fusion protein.

Annealed Sequence 6 (333AG4SA): The oligonucleotide of SEQ ID NO:11 is at the sense side, and the oligonucleotide of SEQ ID NO:12 is at the antisense side.

Annealed Sequence 7 (333AG4S2A): The oligonucleotide of SEQ ID NO:13 is at the sense side, and the oligonucleotide of SEQ ID NO:14 is at the antisense side.

Annealed Sequence 8 (343IG4S2A) The oligonucleotide of SEQ ID NO:15 is at the sense side, and the oligonucleotide of SEQ ID NO:16 is at the antisense side.

Annealed Sequence 9 (333AG4S3A): The oligonucleotide of SEQ ID NO:17 is at the sense side, and the oligonucleotide of SEQ ID NO:18 is at the antisense side.

Annealed Sequence 10 (333AG2A): The oligonucleotide of SEQ ID NO:19 is at the sense side, and the oligonucleotide of SEQ ID NO:20 is at the antisense side.

Annealed Sequence 11 (333AG4A): The oligonucleotide of SEQ ID NO:21 is at the sense side, and the oligonucleotide of SEQ ID NO:22 is at the antisense side.

Annealed Sequence 12 (343IG2A): The oligonucleotide of SEQ ID NO:23 is at the sense side, and the oligonucleotide of SEQ ID NO:24 is at the antisense side.

Annealed Sequence 13 (343IG4A): The oligonucleotide of SEQ ID NO:25 is at the sense side, and the oligonucleotide of SEQ ID NO:26 is at the antisense side.

Annealed Sequence 14 (361SΔA): The oligonucleotide of SEQ ID NO:27 is at the sense side, and the oligonucleotide of SEQ ID NO:28 is at the antisense side.

Annealed Sequence 15 (358DΔA): The oligonucleotide of SEQ ID NO:29 is at the sense side, and the oligonucleotide of SEQ ID NO:30 is at the antisense side.

Annealed Sequence 16 (352TΔA): The oligonucleotide of SEQ ID NO:31 is at the sense side, and the oligonucleotide of SEQ ID NO:32 is at the antisense side.

Annealed Sequence 17 (346RΔA): The oligonucleotide of SEQ ID NO:33 is at the sense side, and the oligonucleotide of SEQ ID NO:34 is at the antisense side.

Annealed Sequence 18 (343IΔA): The oligonucleotide of SEQ ID NO:35 is at the sense side, and the oligonucleotide of SEQ ID NO:36 is at the antisense side.

Annealed Sequence 19 (338KΔA): The oligonucleotide of SEQ ID NO:37 is at the sense side, and the oligonucleotide of SEQ ID NO:38 is at the antisense side.

Annealed Sequence 20 (335TΔA): The oligonucleotide of SEQ ID NO:39 is at the sense side, and the oligonucleotide of SEQ ID NO:40 is at the antisense side.

Annealed Sequence 21 (343IΔP): The oligonucleotide of SEQ ID NO:41 is at the sense side, and the oligonucleotide of SEQ ID NO:42 is at the antisense side.

Annealed Sequence 22 (338KΔP): The oligonucleotide of SEQ ID NO:43 is at the sense side, and the oligonucleotide of SEQ ID NO:44 is at the antisense side.

Annealed Sequence 6 (333AG4SA) expresses a fusion protein formed by linking the N-terminal 333th alanine of IL-6R and the N-terminal 28th alanine of IL-6 through a linker GGGGS (SEQ ID NO:65). Annealed Sequence 7 (333AG4S2A) expresses a fusion protein formed by linking the N-terminal 333th alanine of IL-6R and the N-terminal 28th alanine of IL-6 through a linker GGGGSGGGGS (SEQ ID NO:66). Annealed Sequence 8 (343IG4S2A) expresses a fusion protein formed by linking the N-terminal 343th isoleucine of IL-6R and the N-terminal 28th alanine of IL-6 through a linker GGGGSGGGGS (SEQ ID NO:66). Annealed Sequence 9 (333AG4S3A) expresses a fusion protein formed by linking the N-terminal 333th alanine of IL-6R and the N-terminal 28th alanine of IL-6 through a linker GGGGSGGGGSGGGGS (SEQ ID NO:61). Annealed Sequence 10 (333AG2A) expresses a fusion protein formed by directly linking the N-terminal 333th alanine of IL-6R and the N-terminal 28th alanine of IL-6 through a linker GG. Annealed Sequence 11 (333AG4A) expresses a fusion protein formed by linking the N-terminal 333th alanine of IL-6R and the N-terminal 28th alanine of IL-6 through a linker GGGG (SEQ ID NO:69). Annealed Sequence 12 (343IG2A) expresses a fusion protein formed by linking the N-terminal 343th isoleucine of IL-6R and the N-terminal 28th alanine of IL-6 through a linker GG. Annealed Sequence 13 (343IG4A) expresses a fusion protein formed by linking the N-terminal 343th isoleucine of IL-6R and the N-terminal 28th alanine of IL-6 through a linker GGGG (SEQ ID NO:69). Annealed Sequence 14 (361SΔA) expresses a fusion protein of the present invention formed by linking directly the N-terminal 361th serine of IL-6R and the N-terminal 28th alanine of IL-6 without a linker (SEQ ID NO:70). Annealed Sequence 15 (358DΔA) expresses a fusion protein of the present invention formed by linking directly the N-terminal 358th aspartic acid of IL-6R and the N-terminal 28th alanine of IL-6 without a linker (SEQ ID NO:71). Annealed Sequence 16 (352TΔA) expresses a fusion protein of the present invention formed by directly linking the N-terminal 352th threonine of IL-6R and the N-terminal 28th alanine of IL-6 without a linker (SEQ ID NO:72). Annealed Sequence 17 (346RΔA) expresses a fusion protein of the present invention formed by linking the N-terminal 346th arginine of IL-6R and the N-terminal 28th alanine of IL-6 without a linker (SEQ ID NO:73). Annealed Sequence 18 (343IΔA) expresses a fusion protein of the present invention formed by linking directly the N-terminal 343th isoleucine of IL-6R and the N-terminal 28th alanine of IL-6 without a linker(SEQ ID NO:74). Annealed Sequence 19 (338KΔA) expresses a fusion protein of the present invention formed by linking directly the N-terminal 338th lysine of IL-6R and the N-terminal 28th alanine of IL-6 without a linker (SEQ ID NO:75). Annealed Sequence 20 (335TΔA) expresses a fusion protein of the present invention formed by directly linking the N-terminal 335th threonine of IL-6R and the N-terminal 28th alanine of IL-6 without a linker (SEQ ID NO:76). Annealed Sequence 21 (343IΔP) expresses a fusion protein of the present invention formed by linking the N-terminal 343th isoleucine of IL-6R and the N-terminal 29th proline of IL-6 without a linker (SEQ ID NO:77). Annealed Sequence 22 (338KΔP) expresses a fusion protein of the present invention formed by linking the N-terminal 338th lysine of IL-6R and the N-terminal 29th proline of IL-6 without a linker (SEQ ID NO:78).

The pBS6R6S itself has a gene for coding for the IL-6R-IL-6 fusion protein as an insert. The fusion protein (334LΔV) expressed by this gene is a fusion protein of the present invention formed by linking directly the N-terminal 334th leucine of IL-6R and the N-terminal 30th valine of IL-6 without a linker (SEQ ID NO:79).

Figure 6:
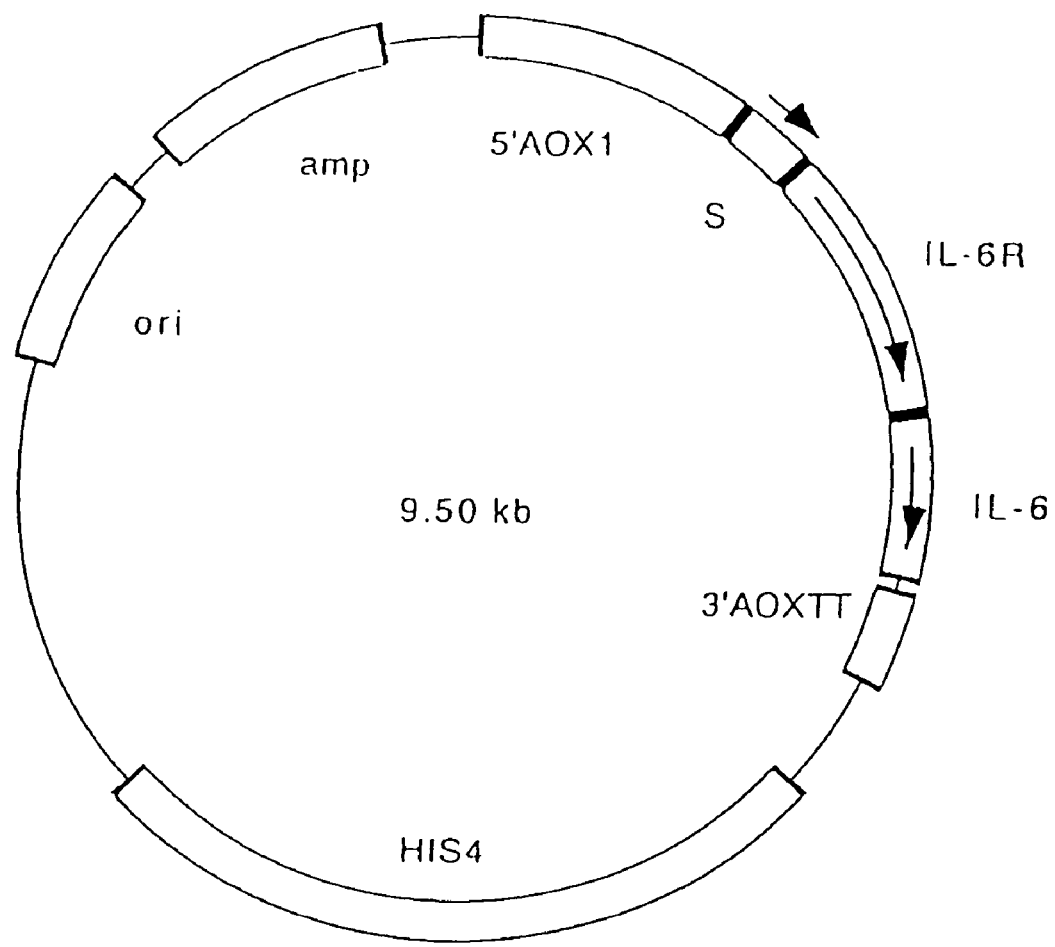
FIG. 6 shows the structure of the plasmid pBS6R6L for expressing a derivative 333AΔA prepared in Example 2.

Finally, the 23 kinds of plasmids obtained above and pBS6R6L were cut respectively by XhoI and NotI to obtain genes for coding for the IL-6R•IL-6 fusion protein. The genes were respectively inserted into pPIC9 having been preliminarily cut by XhoI and NotI to obtain 24 kinds of expression plasmids. FIG. 6 shows the structure of the expression plasmid 333AΔA as an example.

EXAMPLE 3

Preparation of Transformants

From *Pichia pastoris* GS115 strain (Invitrongen Co.), competent cells were prepared by use of an EasyComp Transformation Kit (Invitrogen Co.), and thereto the respective expression plasmids having been linearized by Bgl II were introduced. The transformed cells were cultivated in a minimal nutrient culture medium, and transformed cells having lost the histidine-requiring property were selected.

The obtained transformants were inoculated onto MD plates (1.34% (W/V) of YNB wo AA (Yeast Nitrogen Base Without Amino Acid), 0.00004% (W/V) of biotin, and 2% (W/V) of glucose), and MM plates (1.34% (W/V) of YNB wo AA, 0.00004% (W/V) of biotin, and 0.5% (V/V) of methanol). Thereby, the respective transformants were examined for mut$^+$ and mut$^s$.

Table 1 shows the numbers of the obtained transformants and the numbers of the obtained mut$^s$ strains for the respective derivatives. For the respective derivatives, were obtained the strains transformed by the expression plasmids, average 9.4 in number of mut$^s$ strains (lowest: 4, highest: 17, total: 216).

TABLE 1

| Derivative | Number of obtained transformants | Number of obtained mut$^s$ strain |
| --- | --- | --- |
| 323AG4SA | 60 | 13 |
| 333AG4SA | 149 | 13 |
| 323AG4S2A | 36 | 4 |
| 333AG4S2A | 37 | 9 |
| 343IG4S2A | 65 | 7 |
| 333AG4S3A | 87 | 16 |
| 334LPA | 33 | 13 |
| 333AG2A | 70 | 10 |
| 333AG4A | 49 | 8 |
| 343IG2A | 60 | 7 |
| 343IG4A | 100 | 14 |
| 361SΔA | 23 | 6 |
| 358DΔA | 100 | 7 |
| 352TΔA | 106 | 17 |
| 346RΔA | 54 | 7 |
| 343IΔA | 27 | 10 |
| 343IΔP | 52 | 5 |
| 338KΔA | 93 | 6 |
| 338KΔP | 111 | 11 |
| 334LΔV | 27 | 5 |
| 335TΔA | 92 | 9 |

TABLE 1-continued

| Derivative | Number of obtained transformants | Number of obtained mut$^s$ strain |
|---|---|---|
| 333AΔA | 81 | 11 |
| 323AΔA | 56 | 8 |

EXAMPLE 4

Cultivation of Transformants

The mut$^s$ strains (216 kinds in total), and the mut$^s$ strains which express a fusion protein formed by linking the N-terminal 344th leucine of IL-6R and the N-terminal 28th alanine of IL-6 through a linker SSELV (SEQ ID NO:62) (described in Japanese Patent Application 10-2921) were respectively cultivated at 30° C. for 120 hours in test tubes containing 3 mL of culture medium composed of a BMGY culture medium (1% (W/V) yeast extract, 2% (W/V) peptone, 1.34% (W/V) of YNB wo AA (Yeast Nitrogen Base Without Amino Acid), 0.4 mg/L of biotin, 100 mM potassium phosphate (pH 6.0), and 1% (W/V) of glycerol). At 120 hours of cultivation, a sample was taken out from the respective liquid culture mediums. The samples were respectively centrifuged to obtain a supernatant liquid.

EXAMPLE 5

Measurement of Biological Activity

The biological activity of the IL-6R•IL-6 fusion proteins in the culture supernatant liquids derived in Example 4 was measured by a method employing BAF130 cells. The BAF130 is a cell prepared by transforming a mouse cell BAF not expressing inherently gp130 (Hatakeyama et al.: cell, 63, p. 154, 1989) by introducing a gene for coding for human gp130protein to express this protein. Therefore, this cell exhibits growth activity in the presence of physiologically active IL-6R and IL-6.

Figure 7:
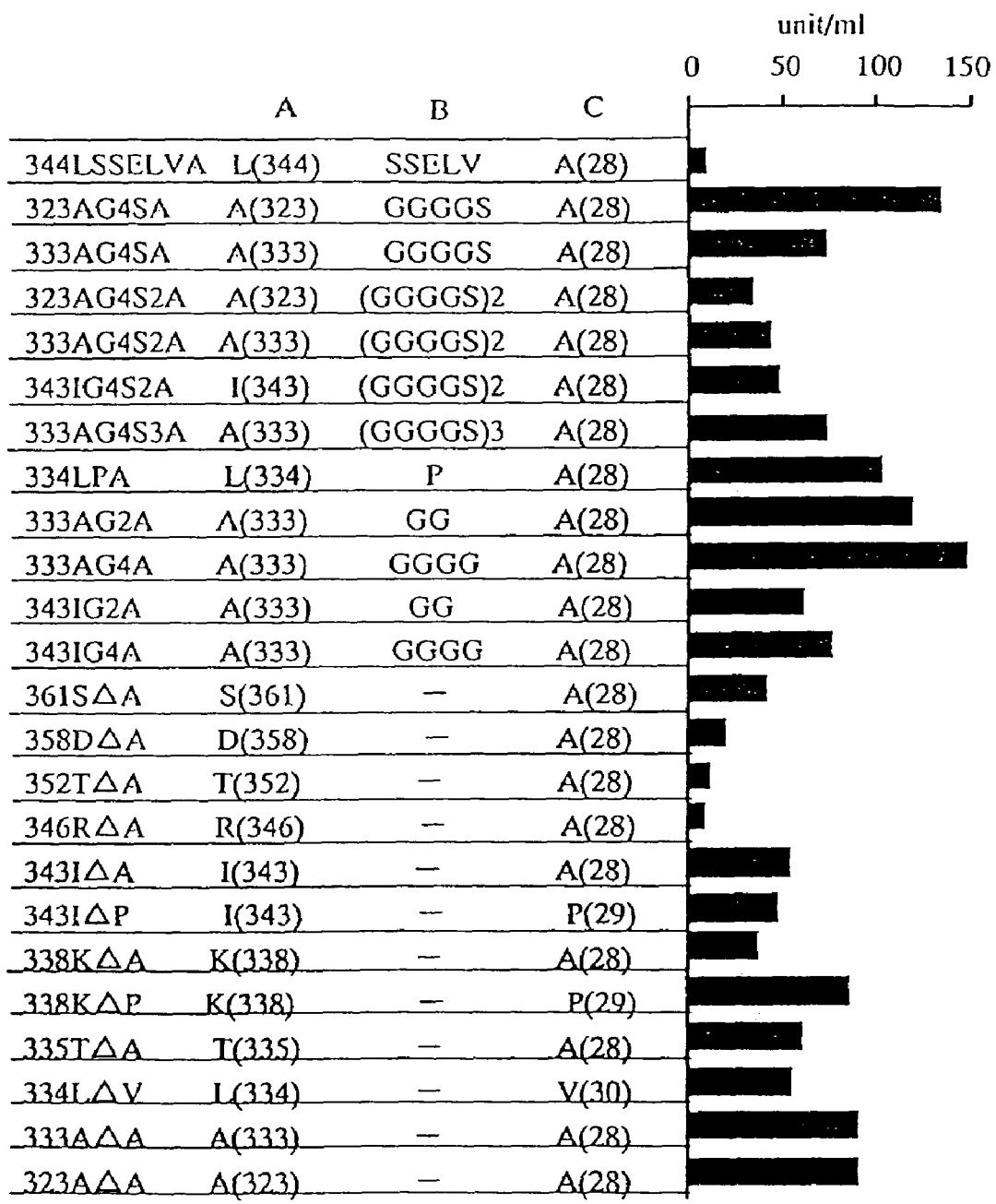
FIG. 7 shows (A) the kind and number of the amino acid at C-terminal of IL-6R region, (B) the amino acid sequence (the symbol "-" means absence of the linker), (C) the kind and number of the amino acid at N-terminal of IL-6R region, (D) the average biological activity for the respective 216 culture medium supernatant liquids derived in Example 4 and measured by the method shown in example 5.

A suspension of BAF130 was placed on 96-well plates in an amount of 2×10$^4$ cells per well. The 216 kinds of culture supernatants were diluted to 1%, 0.25%. 0.061%, and 0.015%, and the fractions of the diluted matters were respectively introduced to the wells. Two days later, the light absorbance was measured at 405 nm with the reference wavelength of 600 nm by use of Cell Counting Kit (produced by Wako Junyaku K. K.). For the standard, 1 µg/mL of IL-6 was diluted to several concentrations and was added with 100 ng/mL of soluble IL-6R in place of the culture supernatant. The activity of the culture supernatant giving the same absorbance dependency on the concentration as this is defined as 1 unit/mL. FIG. 7 shows the average biological activities of the culture supernatants of 4-17 kinds of mut$^s$ strains transformed respectively by the same fusion protein expression vector for each of the fusion proteins.

FIG. 7 shows that, in all of the 12 kinds of fusion proteins having no linker sequence, at least one culture supernatant of the mut$^s$ transformed by the same fusion protein expression vector exhibited the activity. This means that the IL-6R•IL-6 fusion protein of the present invention in which C-terminal of any one of the 39 amino acid residues from N-terminal 323th alanine residue to the N-terminal 361th serine residue is linked to the N-terminal amino acid of IL-6 has a signal transmission property.

FIG. 7 shows also that the fusion proteins 323AΔA, 333AΔA, 334LΔV, 335TΔA, 338KΔP, 338KΔA, 343IΔP, and 343IΔA, which are respectively an IL-6R•IL-6 fusion protein in which the amino acid residue of the N-terminal of IL-6 is linked to C-terminal of the 323th alanine residue, 333th alanine residue, 334th leucine residue, 335th threonine residue, 338th lysine residue, or 343th isoleucine, are more active than the known fusion protein 334LSSELVA (described in Japanese Patent Application No. 10-2921) which is formed by linking the N-terminal 344th leucine of IL-6R and the N-terminal 28th alanine of IL-6 through a linker SSELV.

FIG. 7 further shows that the fusion proteins 323AΔA, 333AΔA, 334LΔV, 335TΔA, 338KΔP, 338KΔA, 343IΔP, or 343IΔA, which are respectively an IL-6RIL-6 fusion protein in which the amino acid residue of N-terminal of IL-6 is linked to the C-terminal of the 323th alanine residue, 333th alanine residue, 334th leucine residue, 335th threonine residue, 338th lysine residue, or 343th isoleucine, are nearly equally active or slightly less active than 323AG4SA, 333AG4SA, 323AG4S2A, 333AG4S2A, 343IG4S2A, and 333AG4S3A which are respectively an IL-6R•IL-6 fusion protein formed by linking with a linker of peptide composed of 5-15 amino acid residues having a high freedom degree like a glycine residue or a serine residue; or 334LPA, 333AG2A, 333AG4A, 343IG2A, and 343IG4A, which are respectively an IL-6R•IL-6 fusion protein formed by linking with a linker of peptide composed of 1-4 amino acids. Therefore, of the IL-6R•IL-6 fusion proteins of the present invention, particularly preferred are those in which the N-terminal amino acid residue of IL-6 is linked to any one of the six amino acid residues of the 323th alanine residue, the 333th alanine residue, the 334th leucine residue, the 335th threonine residue, the 338th lysine residue, and the 343 isoleucine residue.

EXAMPLE 6

Mass Cultivation of mut$^s$ Strains for Expressing Fusion Protein

Figure 8:
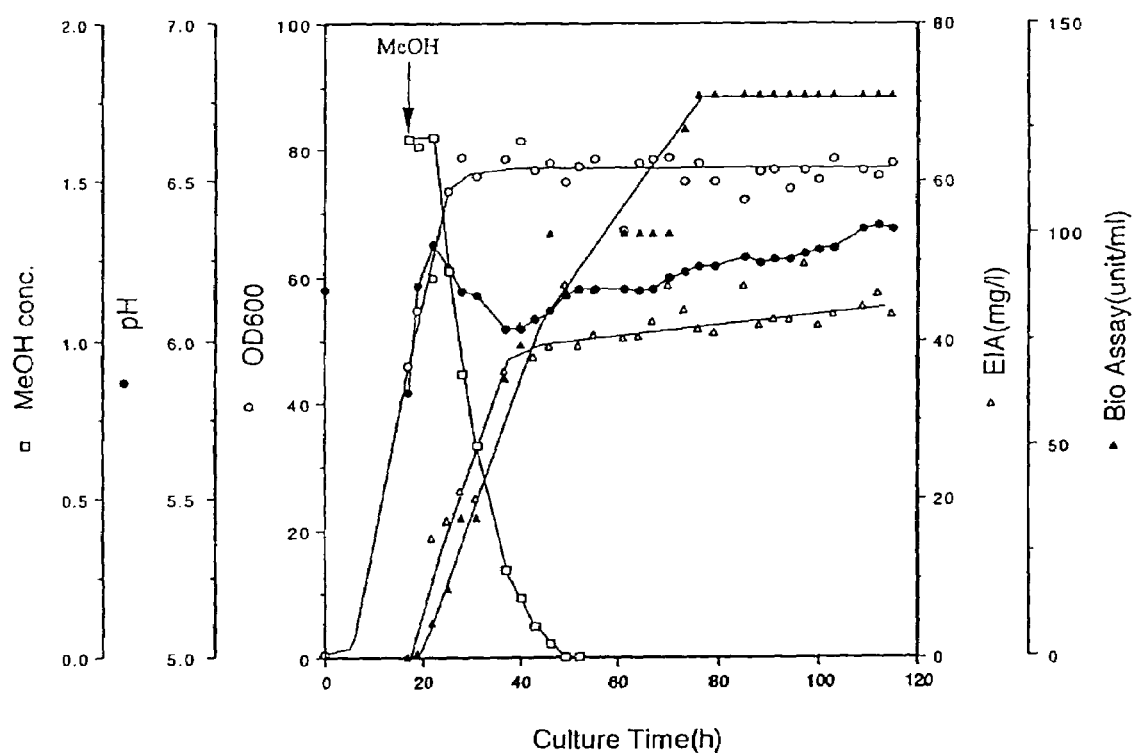
FIG. 8 shows the change caused in the cultivation as shown in Example 6 as a function of the culture time.

Of the eleven mut$^s$ strains expressing 333AΔA described in Example 3, the most active III-108 strain in expression in the method of Examples 4 and 5 was cultivated by use of a 16-liter jar. A glycerol stock of III-108 strain was inoculated into 100 mL of a culture medium BMGY (10 g/L of Bacto Yeast Extract, 20 g/L of Bacto Peptone, 1.34 g/L of Yeast Nitrogen Base without Amino Acid, 100 mM potassium phosphate (pH 6.0), 10 g/L of glycerol, and 0.4 mg/L of biotin), and cultivated at 30° C. for 24 hours by a G-20 Shaking Cultivator (manufactured by NBS Co.) at 200 rpm. The entire culture liquid was inoculated into 8 liters of BMGY (10 g/L of Bacto Yeast Extract, 20 g/L of Bacto Peptone, 1.34 g/L of Yeast Nitrogen Base without Amino Acid, 100 mM potassium phosphate (pH 6.0), 10 g/L of glycerol, and 0.4 mg/L of biotin), and cultivated at 28° C. at stirring rate of 350 rpm and aeration of 1 vvm by a 10-liter jar SF-116 (manufactured by NBS Co.). After 16 hours from the start of the cultivation, was added 1.6 liters of a liquid mixture of 240 mL of methanol, 50 g/L of Bacto Yeast Extract, and 100 g/L of Bacto Peptone to initiate the introduction of expression of a fusion protein. FIG. 8 shows the progress of the cultivation.

The methanol concentration in the liquid culture was monitored by gas chromatography. The pH of the liquid culture was measured by a pH meter. The OD600 value (index of the biomass) was measured by means of a spectrophotometer for a 100-fold dilution of the culture liquid with a physiological saline. The concentration of the fusion protein was measured by sandwich enzyme immunoassay by use of the anti-human IL-6R monochronal antibody MT-18 (Hirato et al.: J. Immunol., vol. 143, 2900 1989) as the solid antibody, the anti-human IL-6 polychronal antibody (produced by Dienzyme Co.) as the detecting antibody, and the purified fusion protein obtained in Example 7 as the standard substance. The biological activity of the fusion protein was measured by use of BAF 130 cells as shown in Example 5.

EXAMPLE 7

Purification of Fusion Protein

The liquid culture picked up in Example 6 was centrifuged to separate the biomass and the supernatant. The supernatant (11.6 L) was diluted with a distilled water to obtain an electric conductivity corresponding to about 50 mM NaCl concentration (66.05 L). Then the pH of the solution was adjusted to 4.5 by acetic acid.

The above diluted solution was introduced to an fluidized adsorption bed, Streamline SP C-50 column, (50 mm ID×100 cm, gel volume 300 mL) having been equilibrated with a 20 mM acetate buffer solution (pH 4.5) (produced by Amasham Pharmacia Co.) from the column bottom upward (linear velocity: 300 cm/hour). After completion of the introduction, the column was washed with the equilbrating buffer solution introduced upward. Then the direction of the liquid introduction was reversed, and an eluting buffer solution (500 mM NaCl, 5% glycerol, 20 mM phosphate buffer solution (pH 6.5)) was introduced downward from the column top (linear velocity 150 cm/hour) to obtain an elution fraction (Streamline elution fraction: 300 mL). The detection of the elution fraction was conducted by measuring the light absorbance at 280 nm.

In the Streamline elution fraction, an ammonium sulfate solution cooled to −20° C. was dissolved to a concentration of 2 M. The solution was introduced to a TSKgel Phenyl-5PW column (21.5 mmID×15 cm, produced by Tosoh Corp.) having been equilibrated with 2M ammonium sulfate solution and 20 mM phosphate buffer solution (pH 6.5) (flow rate: 5 mL/min). After the introduction, the equilibrating buffer solution was introduced there to elute proteins which show weak hydrophobic interaction with the adsorption group. Then the ammonium sulfate concentration in the eluting buffer solution was gradually lowered, and the fraction eluted at a 0.4M ammonium sulfate concentration was collected as the elution fraction of fusion protein (Phenyl-5PW elution fraction, 67 mL). The detection of the fusion protein was conducted by the proliferation activity of BAF 130 cells as the index as shown in Example 5.

The Phenyl-SPW elution fraction was desalted by dialysis with 20 mM acetate buffer solution (pH 4.5) containing 5% glycerol. The desalted solution was introduced to a TSKgel SP-5PW column (7.5 mmID×7.5 cm)(produced by Tosoh Corp.) (flow rate: 2 mL/min) equilibrated with the same buffer solution. After the introduction, the equilibrating buffer solution was allowed to flow to elute proteins less interactive with the adsorption group. Then 20 mM phosphate buffer solution (pH 6.5) containing 500 mM NaCl was allowed to flow (1 mL/min) to obtain a fraction containing the fusion protein at a high concentration (SP-5PW elution fraction, 10 mL). The detection of the fusion protein was conducted by absorbance measurement at 280 nm.

The SP-5PW elution fraction was added portionwise (5 mL every minute) to a TSKgel G3000SW column (21.5 mmID× 30 cm) having been equilibrated with a 20 mM phosphate buffer solution containing 100 mM NaCl (pH 6.5). Thereby the fusion protein was collected by measuring the absorbance at 280 nm.

EXAMPLE 8

Measurement of Activity of Fusion Protein

The fusion protein 333AΔA of the present invention described in Example 5 and purified by the method described in Example 7 (hereinafter referred to as FP6) was used in the experiment below.

Figure 9:
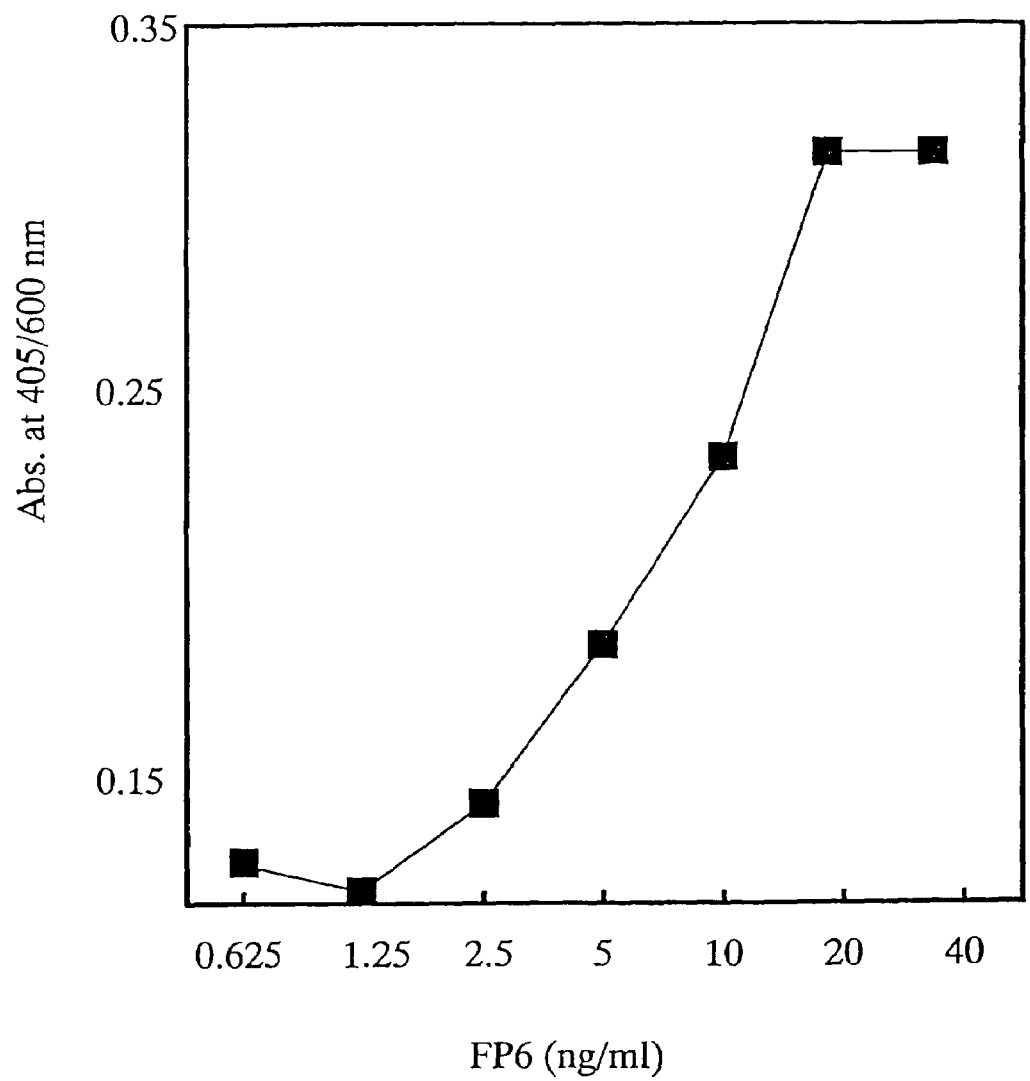
FIG. 9 shows the biological activity of FP6 as measured by the method of Example 8.

The biological activity of FP6 was measured at various concentrations (0.625 to 40 ng/mL) according to the method of measurement of biological activity shown in Example 5 employing BAF130 cells. FIG. 9 shows obviously the concentration dependency of FP6.

Not shown in the drawing, the concentration dependency curve of FP6 derived by diluting the 1 μg/mL FP6 solution to various concentrations (1- to 1024-fold dilution) nearly coincides with the concentration dependency curve of IL-6 derived by diluting the 5 μg/mL solution to various concentrations (1- to 1024-fold dilution). On the other hand, as shown in Example 5, the activity of the culture supernatant giving the same concentration dependency curve as the diluted solution of IL-6 in various concentrations together with 100 ng/mL of soluble IL-6R is defined as one unit/mL. Therefore, 1 μg of FP6 was shown to correspond to 5 units.

EXAMPLE 9

Analysis of Amino Acid Sequence of Fusion Protein

The fusion protein 333AΔA of the present invention described in Example 5 and purified by the method described in Example 7 (hereinafter referred to as FP6) was used in the experiment below.

FP-6 was further purified by reversed phase chromatography with Phenyl-5PW RP column. The elution was conducted with a gradient from 20% acetonitrile/0.1% aqueous trifluoroacetic acid solution to 60% acetonitrile/0.1% aqueous trifluoroacetic acid solution. The obtained fraction was dried up under a reduced pressure. The solid was re-dissolved in aqueous 20% acetonitrile/0.1% trifluoroacetic acid solution, and was analyzed by protein sequencer 477A (manufactured by Applied Biosystem Co.).

Consequently, leucine, alanine, proline, and arginine were detected in this order from the N-terminal, which is consistent with the N-terminal sequence coded by the gene.

EXAMPLE 10

Measurement of Molecular Weight of Sugar Chain Portion of Fusion Protein

The fusion protein 333AΔA of the present invention described in Example 5 and purified by the method described in Example 7 (hereinafter referred to as FP6) was used in the experiment below.

A 150 μL portion of a solution of 0.1% SDS, and 100 mM sodium chloride in 20 mM phosphate buffer solution (pH 6.0) containing 0.1 mg/mL of FP6 was boiled for five minutes, and was cooled by water. A portion of 10 μL of the solution was mixed with a portion of 1 μL of endoglycosidase H of 1 unit/mL (produced by Sigma Co.). The mixtures prepared thus were allowed to react at 25° C., for 30 seconds to 3 hours. The reaction was stopped by addition of 10 μL of 500 mM glycine/hydrochloric acid buffer solution (pH 2.5). Separately, a reference sample of the endoglycosidase H of reaction time of zero minute was provided by mixing successively 10 μL of a 500 mM glycine/hydrochloric acid buffer (pH 2.5), 10 μL of a preliminarily cooled FP6 solution, and 1 μL of endoglycosidase H.

To the solution in which the reaction has been stopped, 3 μL of 72% glycerol and 10% 2-mercaptoethanol colored with bromophenyl blue. This solution was subjected to SDS polyacrylamide gel electrophoresis. After the electrophoresis, the protein in the gel was detected by staining with Coomassie Brilliant Blue R250.

Figure 10:
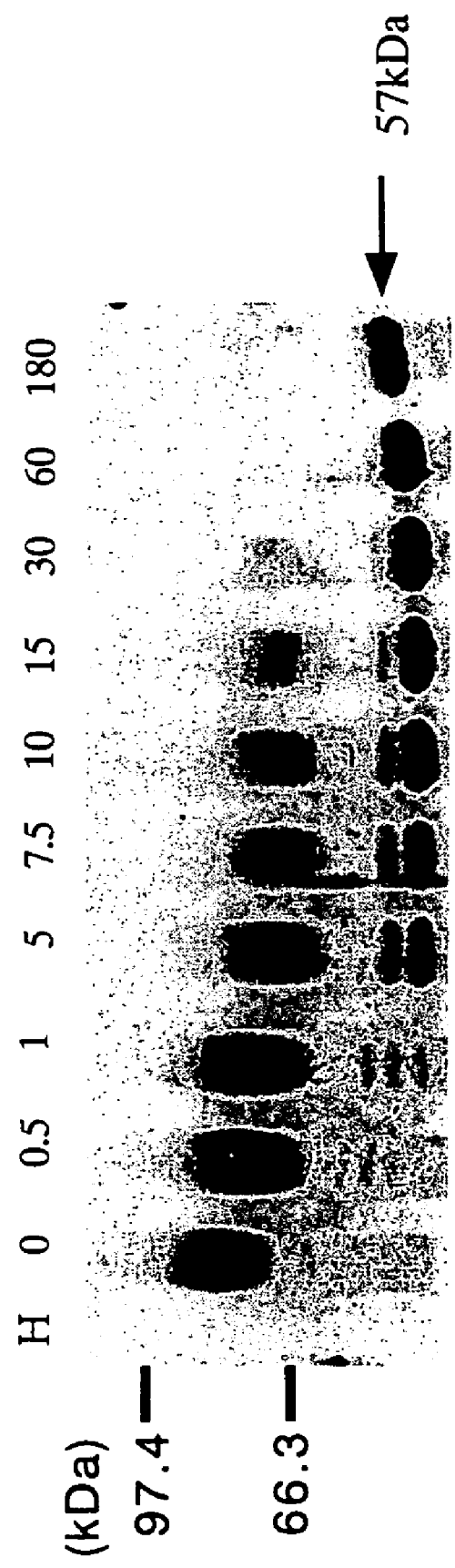
FIG. 10 shows the result of SDS polyacrylamide gel electrophoresis of FP6 having treated by endoglycosidase H for 0 to 180 minutes according to the method shown in Example 10.

As shown clearly in FIG. 10, the FP6 not having reacted with the endoglycosidase H was detected as one bond at the position ranging from 76 to 93 kDa. This means that the molecular weight had a nonuniformity range of 17 kDa. The FP6 having completely digested by the endoglycosidase H was detected at the position of 57 kDa. Not shown in FIG. 9, the FP6 which was denatured with SDS and was reacted with a ten-fold amount of Triton X-100, and N-glycosidase for 18 hours, was detected a the position of 57 kDa. This shows that the molecular weight of the sugar chain bonded by N-glycoside linkage of FP6 ranges from 19 to 36 kDa.

EXAMPLE 11

Effect of Fusion-Protein on Proliferation of Stem Cells

The fusion protein 333AΔA of the present invention described in Example 5 and purified by the method described in Example 7 (hereinafter referred to as FP6) was used in the experiment below.

CD34-positive cells were isolated and purified from 20 mL of human umbilical blood according to the method disclosed in Japanese Patent Application No. 9-325847. The obtained 500 cells were cultivated with 1.2% methylcellulose (Shin-Etsu Kagaku K. K.), 30% bovine serum albumin (Hyclone Laboratories Inc.), 1% bovine serum albumin (hereinafter referred to as BSA) (Sigma Co.), 0.05 mM 2-mercaptoethanol (Sigma Co.), and SCF (stem cell factor) (100 ng/mL) under any of the conditions of (1) combination of IL-6 (100 ng/mL) and IL-6R (100 ng/mL), (2) combination of IL-6 (100 ng/mL) and IL-6R (200 ng/mL), (3) FP6 (300 ng/mL), and (4) FP6 (600 ng/mL), with dispensation of 1 mL fractions of α-MEM (Flow Co.) on a 35-mm plastic cultivation plate (Nunc Co.) for suspension cultivation at 37° C., 5% $CO_2$, and humidity 100%.

Figure 11:
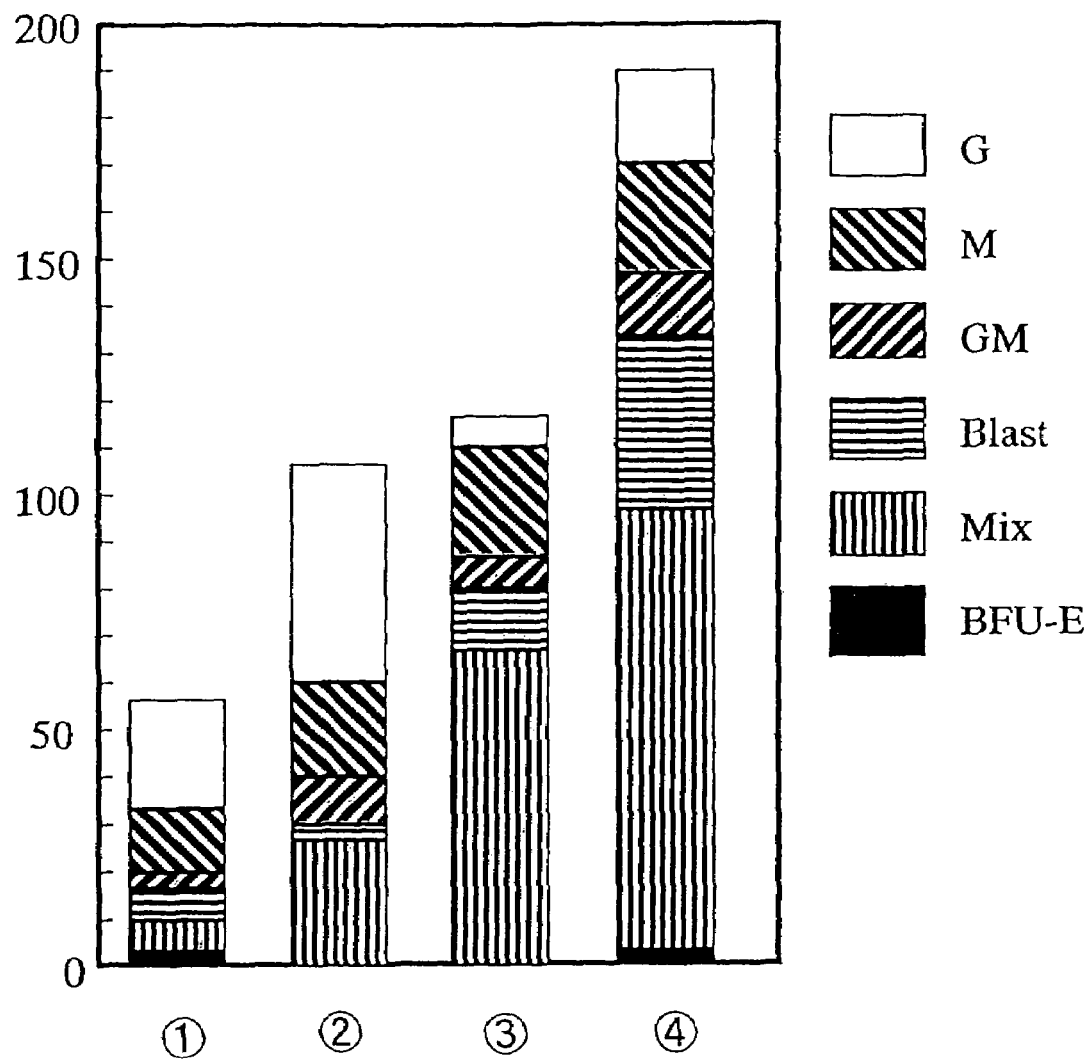
FIG. 11 shows the colony-forming activity of 500 CD34-positive cells by the method of Example 11 with (1) combination of IL-6 (100 ng/mL) and IL-6R (100 ng/mL), (2) combination of IL-6 (100 ng/mL) and IL-6R (200 ng/mL), (3) FP6 (300 ng/mL), and (4) FP-6 (600 ng/mL).

Two weeks later, the colonies were identified by observation with an inverted microscope. FIG. 11 show the results. The colonies were classified into six kinds: a granulocyte colony (G), a macrophage colony (M), granulocyte-macrophage mixed colony (GM), a blast colony (Blast), a granulocyte-macrophage-erythroblast mixed colony (Mix), and erythroblast colony (BFU-E).

As shown in FIG. 11, under the known Conditions (1) and (2), a colony-forming activity was nearly the same as the reported one (Sui et al.: Proc. Natl. Acad. Sci. USA, 92, p. 2589, 1995). On the other hand, under Condition (3) (FP6 (300 ng/mL)) of the present invention, the colony-forming activity was much higher than that of the same concentration of the combination of IL-6 (100 ng/mL) and IL-R (200 ng/mL). Although not shown in the drawing, the sizes of the colonies formed under Condition (3) or (4) of the present invention were remarkably larger than that of the known Condition (1) or (2). This shows that the fusion protein of the present invention has ex vivo proliferation effect for hematopoietic stem cells higher than the known combination of IL-6 with IL-6R.

EXAMPLE 12

Blood Platelet Proliferation Effect of Fusion Protein for Mouse

The fusion protein 333AΔA of the present invention described in Example 5 and purified by the method described in Example 7 (hereinafter referred to as FP6) was used in the experiment below.

Five groups of C57BL6 mouse (male, 8 weeks old), each group having five mice, were employed. The first group mice as an FP6-nondosed group (control group) were dosed with 300 μL of PBS and 1% bovine serum albumin (BSA); the second group mice were dosed with 300 μL of PBS containing 0.5 μg of FP6, and 1% bovine serum albumin (BSA); the third group mice were dosed with 300 μL of PBS containing 1 μg of FP6, and 1% bovine serum albumin (BSA); the fourth group mice were dosed with 300 μL of PBS containing 2 μg of FP6, and 1% bovine serum albumin (BSA); and the fifth group mice were dosed with 300 μL of PBS containing 5 μg of FP6, and 1% bovine serum albumin (BSA). The dose was given to each of the mice intraperitoneally every twelve hours, namely twice a day, for five days. On the sixth day, the mice were exsanguinated from the descending vein. The number of blood platelets was counted by means of a hemocytometer CC-180A (manufactured by Toa Iyou Densi K. K.).

Figure 12:
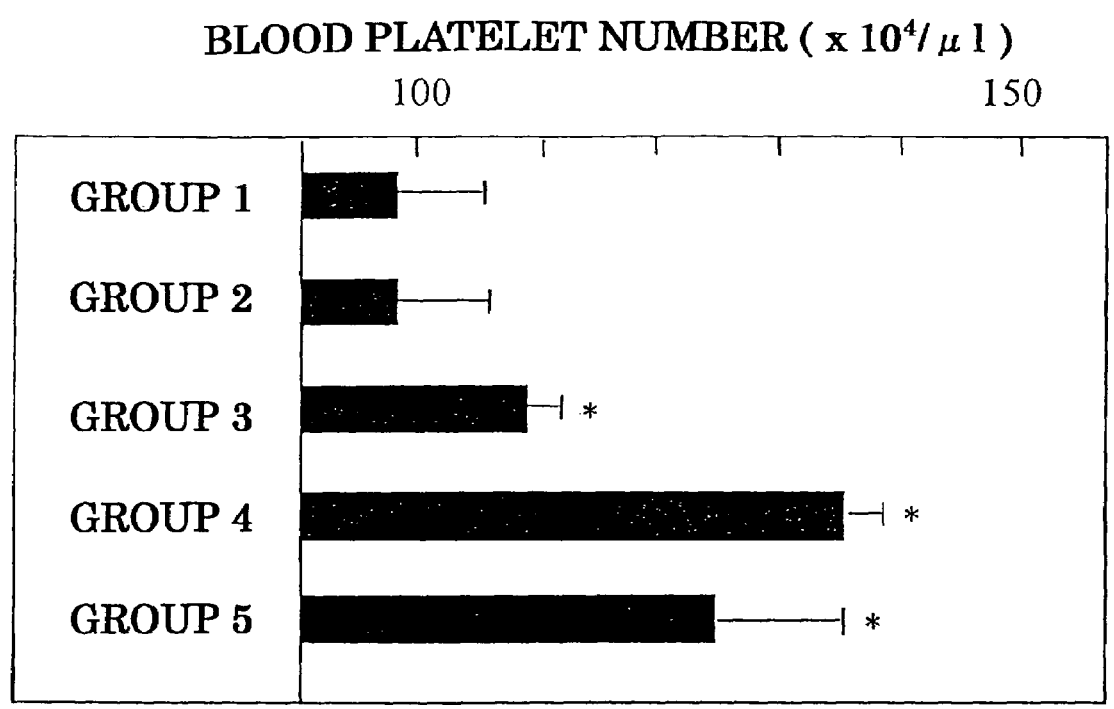
FIG. 12 shows average values of the number of blood platelets of C57BL6 mouse not dosed with FP6 (Group 1), and dosed with FP6 (Groups 2-5) in Example 12.

As shown in FIG. 12, the groups dosed with 1 μg or more of FP6 (third to fifth groups) showed significant proliferation of blood platelets in comparison with the FP6-nondosed group (first group). On the other hand, it is reported that the dose of 0.5 μg of IL-6 (molecular weight: about 21 kDa) having twice number of molecules than 1 μg of FP6 (molecular weight: about 84 kDa) under the same conditions did not cause significant proliferation of blood platelets (Ishibashi et al.: Blood, 74, p. 1241, 1989). This means the higher effect of blood platelet proliferation in vivo of the fusion protein of the present invention in comparison with IL-6.

EXAMPLE 13

Blood Platelet Recovery Effect of Fusion Protein for 5FU-Dosed Mouse

The fusion protein 333AΔA of the present invention described in Example 5 and purified by the method described in Example 7 (hereinafter referred to as FP6) was used in the experiment below.

Two groups of C57BL6 mice (male, 8 weeks old), each group having 15 mice, were employed. The first group mice as an FP6-nondosed group (control group) were dosed with 300 μL of PBS and 1% bovine serum albumin (BSA); and the second group mice were dosed with 300 μL of PBS containing 5 μg of FP6, and 1% bovine serum albumin. All of the mice were dosed with 150 mg/kg of 5FU into the tail vein. The above medical agent was dosed to each of the mouse intraperitoneally every twelve hours, namely twice a day, for five days from the second day to the sixth day. Every day from the seventh day to the ninth day, the five mice of each of the groups were exsanguinated from the descending artery. The number of blood platelets was counted by means of a hemocytometer CC-180A (manufactured by Toa Iyoh Denshi K. K.).

Figure 13:
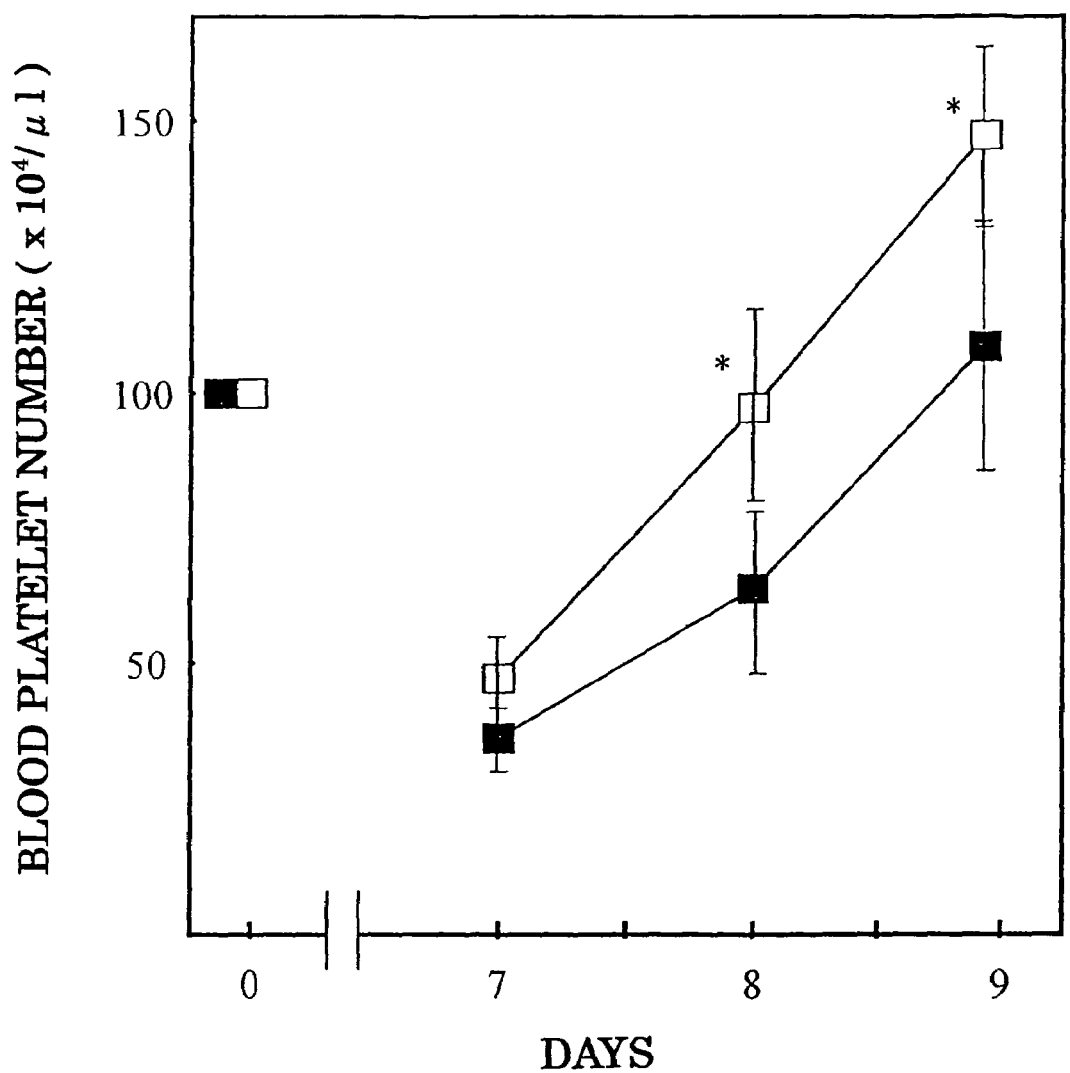
FIG. 13 shows average values of the number of blood platelets of C57BL6 mouse preliminarily dosed with 5FU, and not dosed with FP6 (Group 1, solid squares) and dosed with FP6 (Groups 2, hollow squares) in Example 13.

FIG. 13 shows clearly that the group dosed with FP6 (Second Group) recovered the blood platelets significantly at eighth day and ninth day in comparison with the group not dosed with FP6 (First Group). This means that the fusion protein of the present invention has an effect of recovery in vivo of blood platelet production function having lowered by dose of 5FU.

EXAMPLE 14

Expression of Immunoglobulin-Like Domain-Deficient Type Fusion Protein

An expression plasmid for coding for an IL-6R derivative 112VL (233 amino acids from the N-terminal 112th valine to the N-terminal 344th leucine), and another expression plasmid for coding for an IL-6 derivative 116EL (229 amino acids from the N-terminal 116th glutamic acid to the N-terminal 344th leucine) were constructed as below.

An IL-6R gene (cDNA) was amplified with a primer p6RAB112V (SEQ ID NO:51) and a primer p344F (SEQ ID NO:52), and was cut by XhoI and XbaI. The cut product was inserted into pPIC9 having been cut preliminarily by XhoI and Avr II to obtain pPIC9-112VL.

An IL-6R gene (cDNA) was amplified with a primer p6RAB116E (SEQ ID NO:53) and a primer p344F (SEQ ID NO:54), and was cut by XhoI and XbaI. The cut product was inserted into pPIC9 having been cut preliminarily by XhoI and Avr II to obtain pPIC9-116EL.

An expression plasmid pPIC9-112VAA coding for an immunoglobulin-like domain-deficient type fusion protein (a fusion protein of the present invention having as the N-terminal 112th valine of IL-6R, and the N-terminal 333th alanine of IL-6R and the N-terminal 28th alanine of IR-6 being directly bonded without a linker), and an expression plasmid pPIC9-116EEA coding for the fusion protein 116EAA (a fusion protein of the present invention having as the N-terminal the N-terminal 116th glutamic acid of IL-6R, and the N-terminal 333th alanine of IL-6R and the N-terminal 28th alanine of IR-6 being directly bonded without a linker) were constructed as below.

A fragment obtained by cutting pPIC9-112VL by XhoI and PmaCI was inserted to a 333AΔA-expression plasmid pPIC9-333AA having been preliminarily cut by XhoI and PmaCI to obtain pPIC9-112VAA.

A fragment obtained by cutting pPIC9-116EL by XhoI and PmaCI was inserted to a 333AΔA-expression plasmid pPIC9-333AΔA having been preliminarily cut by XhoI and PmaCI to obtain pPIC9-116EAA.

Transformants were prepared with the above pPIC9-112VAA, and pPIC9-116EAA according to the method shown in Example 3. As the results, 9 mut$^s$ strains for expressing 112VAA and 11 mut$^s$ strains for expressing 116EAA were established. These were cultivated according to the method shown in Example 4, and the biological activity of the liquid supernatant was measured according to the method shown in Example 5.

Figure 14:
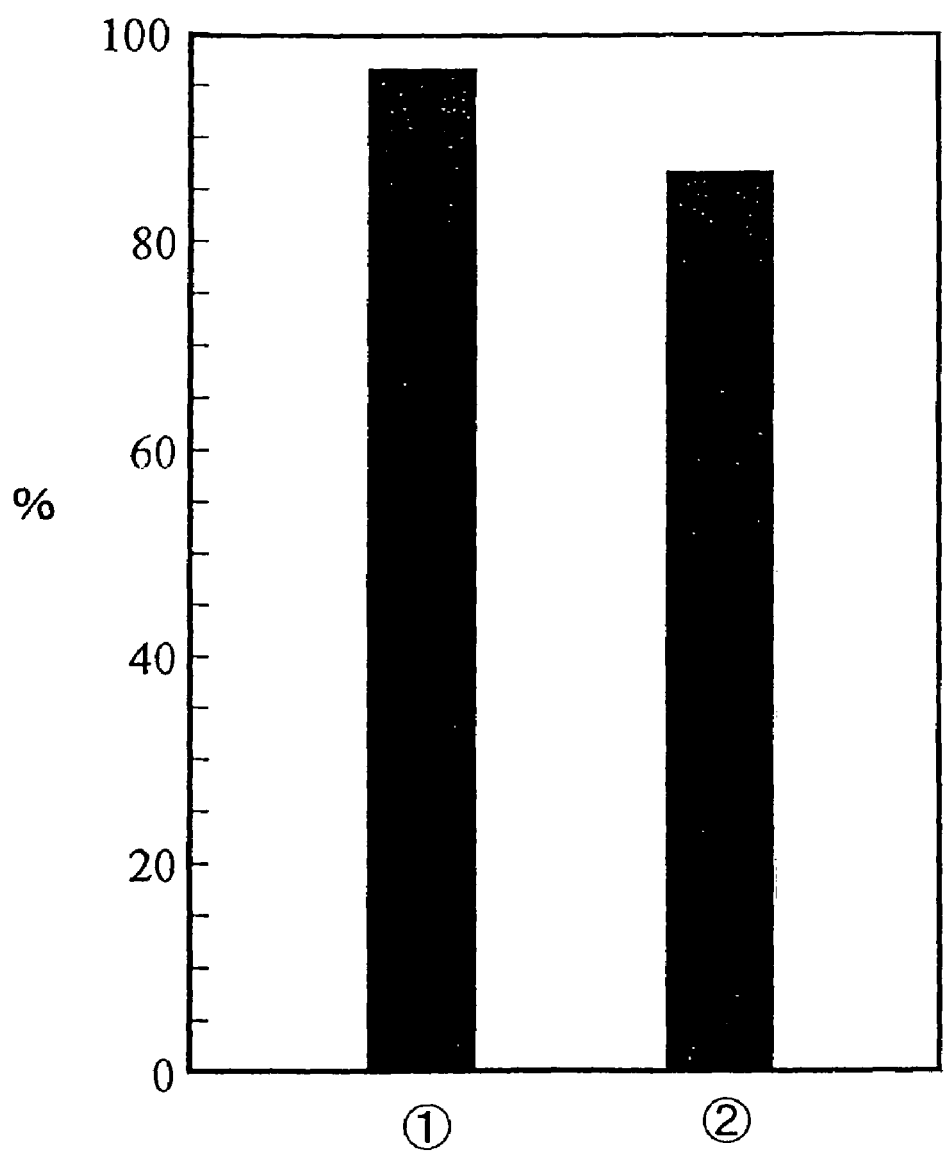
FIG. 14 shows relative average biological activities of (1) nine strains of mut$^s$ capable of expression of fusion protein 112VAA, and (2) 11 strains of mut$^s$ capable of expression of fusion protein 116EAA derived in Example 14 measured according to the method of Example 5 as the relative values (%) to III-108 strain which was the most active of 11 strains of mut$^s$ in expressing 333AΔA.

The immunoglobulin-like domain-deficient fusion proteins 112VAA and 116EAA had the activities nearly equal to the activity of fusion protein 333AΔA having the immunoglobulin-like domain as shown clearly in FIG. 14.

EXAMPLE 15

Determination of the Protease Cutting Site

To 1.9 mL of the Streamline elution fraction derived in Example 7, were added 0.1 mL of 2% SDS, 64% glycerol, and 0.25% bromophenol blue. The mixture was boiled. This was subjected to SDS polyacrylamide gel electrophoresis, and was blotted electrically in 10% methanol/10 mM CAPS buffer solution (pH 11) onto a film of polyvinylidene difluoride (PVDF). The blots were detected by staining with Coomassie Brilliant Blue G-250. The detected protein portions were cut and recovered respectively, and were tested by Protein Sequencer 477A (manufactured by Applied Biosystem Co.). Consequently, the protein of a molecular weight 18 kD was found to be a portion of the fusion protein having aspartic acid residue/valine residue/alanine residue/alanine residue/proline residue/histidine residue, which was produced by cutting of the peptide linkage by a protease of Pichia yeast between the N-terminal 37th lysine residue and the N-terminal 38th aspartic acid residue of IL-6 portion.

EXAMPLE 16

Expression of Protease-Resistant Fusion Protein (1)

From pBS6R6L obtained as in Example 1, IL-6 gene (cDNA) was amplified by using a primer pKN6B38D (SEQ ID NO:55) and a primer pIL6F2 (SEQ ID NO:56), and was cut by NruI and NotI. This was inserted to pBS6R6L having been preliminarily cut by Eco47III and NotI to obtain a plasmid pBS6R6L-38D.

The pBS6R6L-38D was cut by XhoI and NotI to obtain a gene for coding for IL-6R•IL-6 fusion protein, and this was inserted in pPIC9 having been preliminarily cut by XhoI and NotI to obtain an expression plasmid pPIC9-20LAD for coding for a protease-resistant fusion protein 20LAD.

IL-6R gene was amplified by using a primer p6RAB112V (SEQ ID NO:57) and a primer p344F (SEQ ID NO:58), and was cut by XhoI and XbaI. This was inserted to pPIC9 having been preliminarily cut by XhoI and AvrII to obtain a pPIC9-112VL. The pPIC9-112VL was cut by XhoI and PmaCI. The obtained fraction was inserted in pPIC9-20LAA having been preliminarily cut by XhoI and PmaCI. Thereby, an expression plasmid pPIC9-112VAA was prepared which codes for the immunoglobulin-like domain-deficient fusion protein 112VAA (fusion protein having the N-terminal 112th valine of IL-6R as the N-terminal, and directly linked between the N-terminal 333th alanine of IL-6R and the N-terminal 28th alanine of IL-6 without interposition of a linker).

Separately, IL-6R gene was amplified by using a primer p6RAB116E (SEQ ID NO:59) and a primer p344F (SEQ ID NO:58), and was cut by XhoI and XbaI. This was inserted to pPIC9 having been preliminarily cut by XhoI and AvrII to obtain a pPIC9-116EL. The pPIC9-116EL was cut by XhoI and PmaCI. The obtained fraction was inserted in pPIC9-20LAA having been preliminarily cut by XhoI and PmaCI. Thereby, an expression plasmid pPIC9-116EAA was prepared which codes for the immunoglobulin-like domain-deficient fusion protein 116EAA (fusion protein having the N-terminal 116th glutamic acid of IL-6R as the N-terminal, and directly linked between the N-terminal 333th alanine of IL-6R and the N-terminal 28th alanine of IL-6 without interposition of a linker).

The pPIC9-20LAD was cut by XhoI and PmaCI to obtain a gene for coding for IL-6R. This was inserted in pPIC9-112VAA having been preliminarily cut by XhoI and PmaCI to obtain a protease-resistant fusion protein 112VAD of the present invention (fusion protein having the N-terminal 112th valine of IL-6R as the N-terminal, and directly linked between the N-terminal 333th alanine of IL-6R and the N-terminal 38th aspartic acid of IL-6 without interposition of a linker). Separately, the above cut pPIC9-20LAD was inserted in pPIC9-116EAA having been preliminarily cut by XhoI and PmaCI to obtain a protease-resistant fusion protein 116EAD of the present invention (fusion protein having the N-terminal 116th glutamic acid of IL-6R as the N-terminal, and directly bonded between the N-terminal 333th alanine of IL-6R and the N-terminal 38th aspartic acid of IL-6 without interposition of a linker).

EXAMPLE 17

Expression of Protease-Resistant Fusion Protein (2)

The five expression plasmids described in Example 16 (pPIC9-20LAD, pPIC9-112VAA, pPIC9-116EAA, pPIC9-112VAD, and pPIC9-116EAD) were respectively introduced to Pichia yeast according to the method described in Example 3. Consequently, there were obtained 10 strains of $mut^s$ transformed by pPIC9-20LAD, 7 strains of $mut^s$ transformed by pPIC9-112VAA, 10 strains of $mut^s$ transformed by pPIC9-116EAA, 1 strain of $mut^s$ transformed by pPIC9-112VAD, and 6 strains of $mut^s$ transformed by pPIC9-116EAD. These strains were cultivated according to the method described in Example 4, and the supernatant liquids were collected. Their shown in Example 5. Consequently, biologically active were 10 strains out of 10 $mut^s$ strains transformed by pPIC9-20LAD, 7 strains out of 7 $mut^s$ strains transformed by pPIC9-112VAA, 7 strains of 10 $mut^s$ strains transformed by pPIC9-116EAA, 1 strain of 1 $mut^s$ strain transformed by pPIC9-112VAD, and 6 strains out of 6 $mut^s$ strains transformed by pPIC9-116EAD. This means that the deletion of the sequence of the N-terminal 28th alanine to the N-terminal 37th lysine of IL-6 does not affect the biological activity.

EXAMPLE 18

Evaluation of Resistance to Protease

Figure 15:
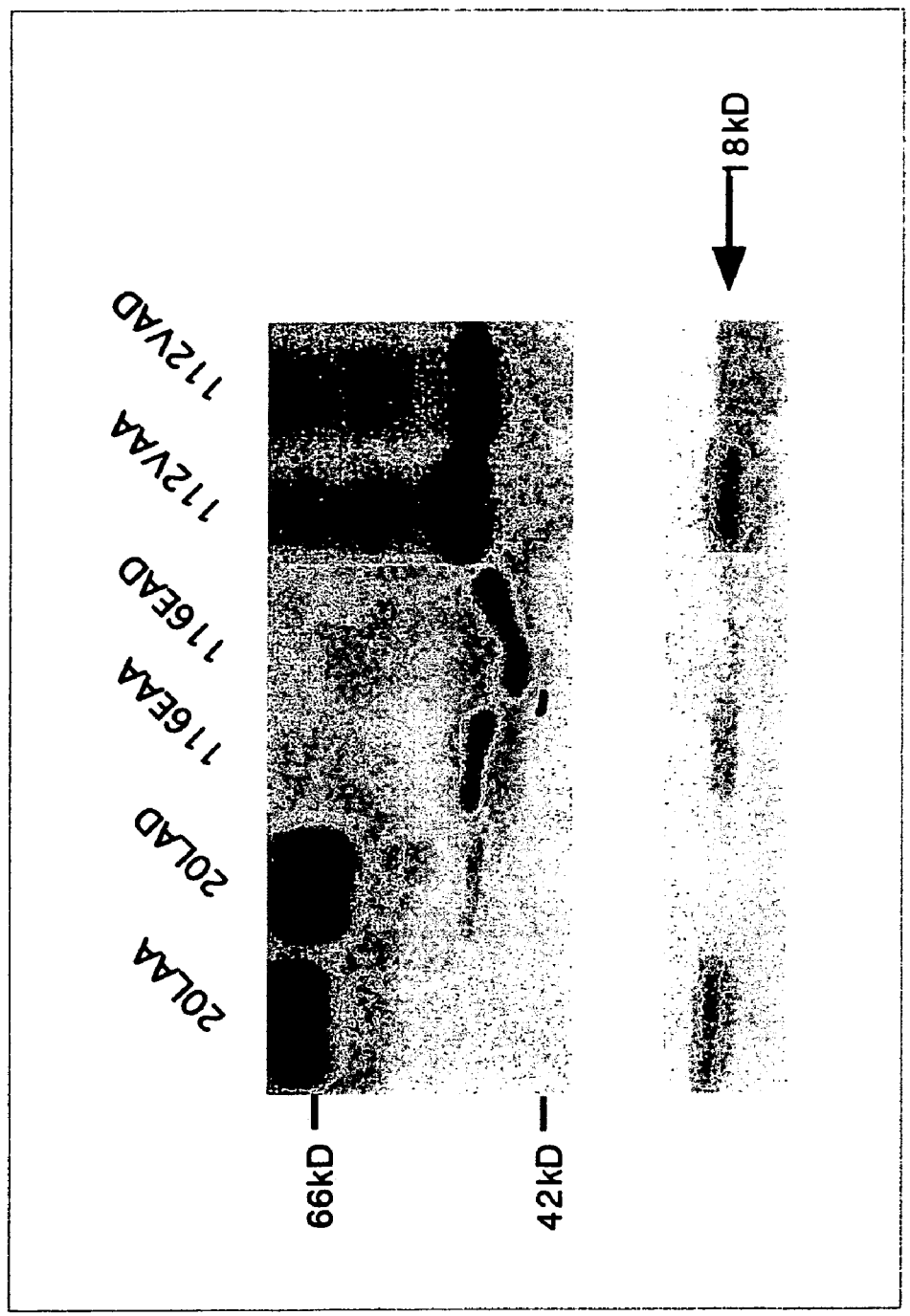
FIG. 15 shows the results of western blotting of culture medium supernatant liquid containing (a) 20LAA, (b) 20LAD, (c) 116EAA, (d) 116EAD, (e) 112VAA, and (f) 112VAD according to the method shown in Example 8.

The transformant strains which express respectively 333AΔA (hereinafter referred to as "20LAA") described in Example 3, and the protease-resistant fusion protein 20LAD of the present invention, the fusion protein 112VAA, the protease-resistant fusion protein 112VAD of the present invention, the fusion protein 116EAA, and the protease-resistant fusion protein 116EAD of the present invention described in Example 17 were cultivated by the method as show below. The cultivation was conducted in a test tube with 3 mL of a BMGY culture medium (1% (W/V) yeast extract, 2% (W/V) peptone, 1.34% (W/V) YNB wo AA, 0.00004% (W/V) biotin, 100 mM potassium phosphate (pH 6.0), and 1% (W/V) glycerol) at 30° C. for 48 hours. The culture was centrifuged to collect the biomass. The biomass pellet was suspended in 2 mL of a BMMY culture medium (1% (W/V) yeast extract, 2% (W/V) peptone, 1.34% (W/V) YNB wo AA, 0.00004% (W/V) biotin, 100 mM potassium phosphate (pH 6.0), and 0.5% (W/V) methanol), and cultivated at 30° C. for 24 hours. At the time of the cultivation for 24 hours, a sample was taken from each of the liquid cultures. The sample was centrifuged to recover the culture supernatant, and the supernatant was subjected to SDS polyacrylamide gel electrophoresis. After the electrophoresis, the proteins in the gel was transferred to a PVDF film, and tested by western blotting with rabbit anti-IL-6 polyclonal antibody (produced by Dienzyme Co.). FIG. 15 shows the results.

As shown in FIG. 15, the band of the molecular weight 18 kD presumably caused by cleavage at the C-terminal of the N-terminal 37th lysine of IL-6 region was detected clearly for 20LAA, 116EAA, and 112VAA, Whereas the band was not detected or hardly detected for the protease-resistant fusion proteins 20LAD, 116EAD, and 112VAD of the present invention. This means that the modification by deletion of the sequence of 10 amino acids from the 28th alanine to the 37th lysine gave the protease resistance.

INDUSTRIAL APPLICABILITY

The IL-6R~IL-6 fusion protein of the present invention having no linker sequence is promising in increasing medical efficacy and lowering remarkably antigenicity. Therefore, this fusion protein is important as a novel remedy in the hematopoiesis field, and is expected in development as an ex vivo amplifier of hematopoietic stem cells and the proliferating agent for blood platelets.

The fusion protein made resistant to the protease secreted by the host cells can be readily mass-produced more efficiently by the reason that the fusion protein dose not cut by the protease in a production process by genetic transformation of host cells, and other reasons. The final production yield can be raised because the fusion protein is not cleaved in a purification process in the presence of the protease. The purification process can be simplified since deactivation of the protease before the purification may be omitted advantageously. Furthermore, the purified product can be more uniform, since contamination of the final purified product by cleaved molecules is not caused.

In addition to the above effects, the substance which is resistant to the protease is expected to retain the biological activity even in the environment in which protease may be present.

The invention claimed is:

1. An IL-6 receptor•IL-6 fusion protein, comprising:
   (A) an IL-6 receptor represented by the amino acid sequence set forth in SEQ ID NO:63 or a partial sequence of IL-6 receptor that binds to IL-6
   wherein the partial sequence of IL-6 receptor has an amino terminus at any one of Leu at the 20$^{th}$ position of SEQ ID NO:63, Val at the 112$^{th}$ position of SEQ ID NO:63, or Glu at the 116$^{th}$ position of SEQ ID NO:63, and a carboxy terminus that corresponds to any one of the amino acids at positions 323 to 361 of SEQ ID NO:63,
   (B) an IL-6 represented by the amino acid sequence of SEQ ID NO:64, or a partial sequence of IL-6 that binds to the IL-6 receptor of (A)
   wherein the partial sequence of IL-6 has an amino terminus at any one of Ala at the 28$^{th}$ position of SEQ ID NO:64, Pro at the 29$^{th}$ position of SEQ ID NO:64, Val at the 30$^{th}$ position of SEQ ID NO:64, or Asp at the 38$^{th}$ position of SEQ ID NO:64, and a carboxy terminus at Met at the 212$^{th}$ position of SEQ ID NO:64;
   wherein (A) and (B) are linked via a peptide bond from the carboxy terminus of (A) to the amino terminus of (B)—, and
   wherein said fusion protein induces gp130 for signal transmission.

2. The IL-6 receptor•IL-6 fusion protein of claim 1, wherein the amino acid at the carboxy terminus of (A) is any one of the Ala at the 323$^{rd}$ position of SEQ ID NO:63, Ala at the 333$^{rd}$ position of SEQ ID NO:63, Leu at the 334$^{th}$ position of SEQ ID NO:63, Thr at the 335$^{th}$ position of SEQ ID NO:63, Lys at the 338$^{th}$ position of SEQ ID NO:63, or Ile at the 343$^{rd}$ position of SEQ ID NO:63.

3. An ex vivo amplifier for hematopoietic stem cells, comprising:
   (A) an IL-6 receptor represented by the amino acid sequence set forth in SEQ ID NO:63 or a partial sequence of IL-6 receptor that binds to IL-6
   wherein the partial sequence of IL-6 receptor has an amino terminus at any one of Leu at the 20$^{th}$ position of SEQ ID NO:63, Val at the 112$^{th}$ position of SEQ ID NO:63, or Glu at the 116$^{th}$ position of SEQ ID NO:63, and a carboxy terminus at any one of the amino acids at positions 323 to 361 of SEQ ID NO:63,
   (B) an IL-6 represented by the amino acid sequence of SEQ ID NO:64, or a partial sequence of IL-6 that binds to the IL-6 receptor of (A)
   wherein the partial sequence of IL-6 has an amino terminus at any one of Ala at the 28$^{th}$ position of SEQ ID NO:64, Pro at the 29th position of SEQ ID NO:64 Val at the 30$^{th}$ position of SEQ ID NO:64, or Asp at the 38$^{th}$ position of SEQ ID NO:64, and a carboxy terminus at Met at the 212$^{th}$ position of SEQ ID NO:64;
   wherein (A) and (B) are linked via a peptide bond from the carboxy terminus of (A) to the amino terminus of (B),
   wherein said amplifier induces proliferation of hematopoietic stem cells.

4. The ex vivo amplifier for hematopoietic stem cells of claim 3, wherein the amino acid at the carboxy terminus is (A) any one of Ala at the 323$^{rd}$ position of SEQ ID NO:63, Ala at the 333$^{rd}$ position of SEQ ID NO:63, Leu at the 334$^{th}$ position of SEQ ID NO:63, Thr at the 335$^{th}$ position of SEQ ID NO:63, Lys at the 338$^{th}$ position of SEQ ID NO:63, or Ile at the 343$^{rd}$ position of SEQ ID NO:63.

5. A blood platelet proliferating agent, comprising:
   (A) an IL-6 receptor represented by the amino acid sequence set forth in SEQ ID NO:63-or-a partial sequence of IL-6 receptor that binds to IL-6
   wherein the partial sequence of IL-6 receptor has an amino terminus at any one of Leu at the 20$^{th}$ position of SEQ ID NO:63, Val at the 112$^{th}$ position of SEQ ID NO:63, or Glu at the 116$^{th}$ position of SEQ ID NO:63, and a carboxy terminus that corresponds to any one of the amino acids at positions 323 to 361 of SEQ ID NO:63,
   (B) an IL-6 represented by the amino acid sequence of SEQ ID NO:64, or a partial sequence of IL-6 that binds to the IL-6 receptor of (A)
   wherein the partial sequence of IL-6 has an amino terminus at any one of Ala at the 28$^{th}$ position of SEQ ID NO:64, Pro at the 29$^{th}$ position of SEQ ID NO:64, Val at the 30$^{th}$ position of SEQ ID NO:64, or Asp at the 38$^{th}$ position of SEQ ID NO:64, and a carboxy terminus at Met at the 212$^{th}$ position of SEQ ID NO:64;
   wherein (A) and (B) are directly linked via a peptide bond from the carboxy terminus of (A) to the amino terminus of (B),
   wherein said agent induces proliferation in blood platelets.

6. The blood platelet proliferating agent of claim 5, wherein the amino acid at the carboxy terminus of (A) is any one of Ala at the 323$^{rd}$ position of SEQ ID NO:63, Ala at the 333$^{rd}$ position of SEQ ID NO:63, Leu at the 334$^{th}$ position of SEQ ID NO:63, Thr at the 335$^{th}$ position of SEQ ID NO:63, Lys at the 338$^{th}$ position of SEQ ID NO:63, or Ile at the 343$^{rd}$ position of SEQ ID NO:63.

* * * * *